(12) United States Patent
Jeong et al.

(10) Patent No.: US 8,636,843 B2
(45) Date of Patent: Jan. 28, 2014

(54) SINGLE-CRYSTAL APATITE NANOWIRES SHEATHED IN GRAPHITIC SHELLS AND SYNTHESIS METHOD THEREOF

(75) Inventors: Nam Jo Jeong, Daejeon (KR); Jung Hoon Lee, Seoul (KR)

(73) Assignee: Korea Institute of Energy Research, Daejeon (KR)

( * ) Notice: Subject to any disclaimer, the term of this patent is extended or adjusted under 35 U.S.C. 154(b) by 3 days.

(21) Appl. No.: 13/506,253

(22) Filed: Apr. 6, 2012

(65) Prior Publication Data

US 2012/0258308 A1     Oct. 11, 2012

(30) Foreign Application Priority Data

Apr. 7, 2011    (KR) .................... 10-2011-0031977
Jun. 14, 2011   (KR) .................... 10-2011-0057472
Sep. 23, 2011   (KR) .................... 10-2011-0096329

(51) Int. Cl.
    *C30B 25/00*    (2006.01)
(52) U.S. Cl.
    USPC ............... 117/87; 117/84; 117/88; 117/104; 117/903; 117/920; 117/921; 117/929
(58) Field of Classification Search
    USPC ......... 117/84, 87, 88, 104.903, 920, 921, 929
    See application file for complete search history.

(56) References Cited

U.S. PATENT DOCUMENTS

| 7,879,388 | B2 | 2/2011 | Clarkson et al. | |
| 2002/0172820 | A1* | 11/2002 | Majumdar et al. | 428/357 |
| 2007/0154385 | A1* | 7/2007 | Min et al. | 423/622 |

FOREIGN PATENT DOCUMENTS

| EP | 2508471 A3 | 12/2012 |
| JP | 2006219307 A * | 8/2006 |
| JP | 2007039623 A * | 2/2007 |
| JP | 2008-214688 A | 9/2008 |
| KR | 10-2006-0097939 A | 9/2006 |
| KR | 10-2008-0043542 A | 5/2008 |
| KR | 10-2010-0096812 A | 9/2010 |
| KR | 10-2010-0136185 A | 12/2010 |

OTHER PUBLICATIONS

KIPO Notice of Allowance for Korean Patent Application No. 10-2011-0031977 which corresponds to the above identified U.S. Appl. No. 13/506,253.

Y. Chen et al., "Carbon Nanotube Reinforced Hydroxyapatite Composite Coatings Produced Through Laser Surface Alloying", Science Direct, Carbon 44, 2006, pp. 37-45.

* cited by examiner

*Primary Examiner* — Matthew Song
(74) *Attorney, Agent, or Firm* — LRK Patent Law Firm

(57) ABSTRACT

Heterogeneous nanowires having a core-shell structure consisting of single-crystal apatite as the core and graphitic layers as the shell and a synthesis method thereof are provided. More specifically, provided is a method capable of producing large amounts of heterogeneous nanowires, composed of graphitic shells and apatite cores, in a reproducible manner, by preparing a substrate including an element corresponding to X of $X_6(YO_4)_3Z$ which is a chemical formula for apatite, adding to the substrate a gaseous source containing an element corresponding to Y of the chemical formula, adding thereto a gaseous carbon source, and allowing these reactants to react under optimized synthesis conditions using chemical vapor deposition (CVD), and to a method capable of freely controlling the structure and size of the heterogeneous nanowires and also to heterogeneous nanowires synthesized thereby.

13 Claims, 22 Drawing Sheets
(17 of 22 Drawing Sheet(s) Filed in Color)

SINGLE-CRYSTAL APATITE NANOWIRES SHEATHED IN GRAPHITIC SHELLS AND SYNTHESIS METHOD THEREOF

BACKGROUND OF THE INVENTION

1. Field of the Invention

The present invention relates to heterogeneous nanowires having a core-shell structure consisting of single-crystal apatite as the core and graphitic layers as the shell and to a synthesis method thereof. More specifically, the present invention relates to a method capable of producing large amounts of heterogeneous nanowires, composed of graphitic shells and apatite cores, in a reproducible manner, by preparing a substrate including an element corresponding to X of $X_5(YO_4)_3Z$ which is a chemical formula for apatite, adding to the substrate a gaseous source containing an element corresponding to Y of the chemical formula, adding thereto a gaseous carbon source, and allowing these reactants to react under optimized synthesis conditions using chemical vapor deposition (CVD), and to a method capable of freely controlling the structure and size of the heterogeneous nanowires and also to heterogeneous nanowires synthesized thereby. The examples of the present invention show the results of using calcium or strontium as an element corresponding to X of the chemical formula, the results of using phosphine containing phosphorus for the formation of Y of the chemical formula, and the results of using acetylene ($C_2H_2$), methane ($CH_4$), ethylene ($C_2H_4$) or propane ($C_3H_8$) as a gaseous carbon source for the formation of graphitic layers.

2. Description of the Prior Art

Crystalline carbon materials such as graphene are known as advanced materials having very excellent electrical, mechanical, chemical and physical properties and have recently been used in a wide range of applications, including electrode materials, reinforced composite materials, and optical materials.

Carbon nanowires are advanced materials having a shell structure consisting of graphene rolled up into a cylinder shape having a diameter of nanometer order and can be broadly classified into carbon nanotubes, carbon nanofibers, and carbon nanocables. Carbon nanocables generally refer to structures in which materials having the shape of rods or wires are included in the hollow spaces of graphitic shells, unlike carbon nanotubes or carbon nanowires.

When the material included in such carbon nanocable structures to form the core is disadvantageous that it is sensitive to external environmental factors (for example, it is easily to be oxidized, or is adversely affected by acid or is sensitive to water), or the mechanical and physical properties are inherently weak or the electrical properties thereof are not excellent, the graphitic shells surrounding the surface of the core materials can overcome such disadvantages, and thus are highly beneficial.

In addition to the fact that the inherent properties of the core material can be maintained by the graphitic shells, the properties of the core material which is very excellent in one of the electrical, mechanical, chemical and physical properties can be additionally improved by the graphitic shells.

Meanwhile, carbon nanocable structures can be formed by various methods. The most general method is an in-situ formation method that is based on chemical vapor deposition (CVD) or arc discharge. In this method, cores which can be present in carbon nanotubes are made mainly of transition metals having an excellent catalytic activity of forming carbon nanotubes. In recent years, nanosized metal oxides have been reported to be able to form such graphitic shells. The vapor-liquid-solid (VLS) growth mechanism is primarily responsible for the synthesis of carbon nanocables by the above method.

Another method is a method of filling a liquid or gaseous material into prepared carbon nanotube structures using capillary action, a wet-chemical method, and a nano-filling reaction. In this method, mass production is not easier than in the in-situ formation method, but there is an advantage in that various materials can be used as the core material.

Meanwhile, it has not yet been reported that bio-minerals such as apatite can be formed directly into carbon nanotube structures which comprise, for example, graphitic shells. Calcium phosphate compounds are typical minerals and can typically be developed to the chemical structure of apatite, which is generally represented by $X_8(YO_4)_3(Z)$, wherein X may represent Ca, K, Na, Sr, Ba, Mg, Pb, Cb or Zn, Y may represent P, As, V or S, and Z may represent $OH^-$, $F^-$, $CO_3^-$ or $Cl^-$. Compounds represented by the chemical formula have various properties and structures depending the components and composition ratios of X, Y and Z.

Particularly, compounds in which X is Ca and Y is P are calcium phosphate compounds which have various properties and structures depending on whether Z represents $OH^-$, $F^-$, $O^-$, $CO_3^-$ or $Cl^-$. Specific examples of the calcium phosphate compounds include hydroxyapatite: HA(Ca/p=1.67)-$Ca_5(PO_4)_3(OH)$; fluoroapatite: (Ca/p=1.67)-$Ca_5(PO_4)_3(F)$; carbonated apatite: (Ca/p=1.67)-$Ca_n(PO_4)_8(CO_3)(OH)$, oxyapatite: OA(Ca/p=1.67)-$Ca_{10}(PO_4)_6O$; octacalcium phosphate: OCP(Ca/p=1.33)-$Ca_8H_2(PO_4)_65(H_2O)$; tricalcium phosphate: OCP(Ca/p=1.5)-$Ca_3(PO_4)_2$; tetracalcium phosphate: OCP(Ca/p=2.0)-$Ca_4(PO_4)_2O$; brushite: (Ca/p=1.0)-$CaH(PO_4)2(H_2O)$; and monetite: (Ca/p=1.0)-$CaH(PO_4)$).

These compounds generally have very excellent biocompatibility and are used mainly in the biotechnology field related to the production of artificial teeth and bones, but are known to have low mechanical strength and insufficient electrical and chemical properties.

In addition, the synthesis of calcium phosphate compounds is generally carried out in a moisture- or oxygen-rich atmosphere because of their structural characteristics. Such conditions for the synthesis of calcium phosphate compounds are significantly inconsistent with conditions for the production of graphitic structure, and thus two kinds of materials (graphitic shells and calcium phosphate compounds) were difficult to synthesize simultaneously under the same conditions. Accordingly, there is a need to form composites of calcium phosphate compounds and graphitic nanostructures, thereby improving the mechanical and physical properties of the calcium phosphate compounds.

SUMMARY OF THE INVENTION

It is an object of the present invention to provide novel heterogeneous nanowires, which have a core-shell structure consisting of apatite as the core and graphitic layers as the shell, and thus show very excellent electrical, mechanical, chemical, physical and biocompatible properties, and a synthesis method thereof.

Another object of the present invention is to provide heterogeneous nanowires and a synthesis method thereof, in which an apatite core and a graphitic shell can be produced simultaneously by a single process and the shapes thereof can be freely controlled.

Still another object of the present invention is to provide heterogeneous nanowires which can be applied in all the technical fields, including the energy field and the nano/biotechnology field, in which apatite and graphitic shells are used, and a synthesis method thereof.

To achieve the above objects, the present invention provides a method for synthesizing single-crystal apatite nanowires sheathed in graphitic shells, the method comprising the steps of: i) introducing into a reactor either a material containing an element corresponding to X of $X_5(YO_4)_3(Z)$, which is a chemical formula for apatite, or a substrate containing the material; ii) maintaining the inside of the reactor in a vacuum and supplying a carrier gas to the reactor; iii) increasing the temperature of the reactor to synthesis temperature; iv) supplying reactant gases comprising carbon and phosphorus sources to the reactor and allowing the reactant gases to react with the material or substrate introduced into the reactor in step i); and v) cooling the reactor to room temperature in a carrier gas atmosphere.

In the method of the present invention, the element corresponding to X in the chemical formula may be Ca, K, Na, Sr, Ba, Mg, Pb, Cb or Zn. For example, if the element is calcium, the material containing the element is preferably a material which contains calcium or calcium oxide or is capable of inducing calcium or calcium oxide. Examples of a biomaterial containing calcium include henequen and kenaf, which are woody biomasses, red algae and brown seaweed.

The shape of the substrate may be selected from mesh, foams, spheres, fibers, tubes, plates, thin films, powders, and nanoparticles. In one embodiment of the present invention, the substrate may be glass fiber or glass powder.

In addition, the substrate is preferably mounted in the reactor using an assistant material made of alumina or quartz which is stable to the reactant gases at a temperature ranging from room temperature to 1000° C. Furthermore, before the reactant gases are supplied, the internal pressure of the reactor is reduced to a vacuum of $1 \times 10^{-3}$ Torr by, means of a vacuum pump in order to remove the remaining gas from the reactor, and then the carrier gas is supplied to the reactor maintained in a vacuum.

Moreover, the carrier gas includes any one of argon, helium and nitrogen. Before the reactant gases are supplied, the temperature of the reactor is preferably controlled to the synthesis temperature ranging from 500° C. to 1000° C.

Also, the carbon source-containing reactant gas that is supplied to the temperature-controlled reactor preferably includes hydrocarbon gas such as acetylene, ethylene ethane, propane or methane, and the phosphorus source-containing reactant gas preferably includes phosphine gas.

Herein, the phosphine gas is one example of a reactant gas that contains phosphorus (P) among P, As, V and S, which are elements corresponding to Y in the apatite structure.

Also, the carbon source-containing reactant gas is supplied in order to form graphitic shells.

The reactant gases can react with each other during the synthesis process to form new gaseous carbon-phosphorus organic compounds. If the carbon-phosphorus organic compounds are prepared in liquid form, they are preferably evaporated by heating or atomized by ultrasonic atomization, before they are supplied to the reactor.

If the introduced substrate is a calcium-containing substrate, amorphous calcium phosphate nanoparticles start to be formed on the surface of the substrate as phosphine is supplied. In this process, phosphorus molecules thermally decomposed from phosphine at synthesis temperature react with the oxygen of the substrate to form phosphates which then react with calcium, thereby forming amorphous calcium phosphate nanoparticles. In addition, because the gaseous carbon-phosphate organic compounds resulting from the reaction between the carbon and the phosphorus source-containing reactant gas can induce the strong bonding between the calcium and the phosphate, they can also promote the formation of amorphous calcium phosphate nanoparticles. Then, the amorphous calcium phosphate nanoparticles undergo a nucleation and crystallization process, and the gaseous carbon-phosphorus organic compounds also play a role in promoting this nucleation and crystallization process and function to induce the apatite crystal to be oriented in one plane that is the (001) plane. When the phosphorus and calcium-containing gaseous species are continuously supplied, one-dimensional apatite nanowires oriented in the (001) plane grow, while graphitic shells are formed around the surface of the grown apatite nanowires under supply of the carbon source-containing reactant gas. The graphitic shells formed around the apatite nanowires function to block the phosphorus and calcium-containing gaseous species from being supplied to the radial surface of the nanowires, thereby preventing the lateral growth of the nanowires. In addition, the formed graphitic shells function to promote the growth of the nanowire in the axial direction. As a result, the inventive apatite nanowires sheathed in graphitic shells can be formed by a CVD-based vapor-solid (VS) growth mechanism. In this formation process, the gaseous carbon-phosphorus organic compounds can play a very important role in the formation and oriented growth of apatite crystals.

In addition, the time of the reaction is preferably controlled within the range of 30 seconds to 2 hours.

In another aspect, the present invention provides single-crystal apatite nanowires sheathed in graphitic shells, synthesized by the above-described method. In a preferred embodiment, apatite comprises 99-100% of the hollow volume of the graphitic shells, the nanowires have a diameter of 5 nm to 20 nm and a length of 100 nm to 5 μm, and the graphitic shells have a thickness of 0.34 to 2 nm. The heterogeneous nanowires may be used as biomaterials, nanomaterials, or nano/bio composite materials.

In still another aspect, the present invention provides a method for synthesizing heterogeneous nanowires, which are composed of graphitic shells and apatite cores and have a thickness which changes in the axial direction thereof, the method comprising the steps of: i) introducing into a reactor either a material containing an element corresponding to X of $X_5(YO_4)_3(Z)$, which is a chemical formula for apatite, or a substrate containing the material; ii) maintaining the inside of the reactor in a vacuum and supplying a carrier gas to the reactor; iii) increasing the temperature of the reactor to synthesis temperature; iv) supplying reactant gases comprising carbon and phosphorus sources into the reactor and allowing the reactant gases to react with the material or substrate, introduced into the reactor in step i); v) controlling any one or more of the temperature of the reaction between the reactant gases and the substrate, the reaction time, and the concentration of the carbon or phosphorus-containing reactant gases, thereby controlling the shape of the heterogeneous nanowires being synthesized; and vi) cooling the reactor to room temperature in a carrier gas atmosphere.

In the step of allowing the reactant gases to react with the substrate material, the supply rate of the gaseous carbon or phosphorus source can be controlled, whereby the nanowires can have knot-like portions which change the thickness of nanowires along the axial direction of the nanowires. Herein, the supply rate of the carbon and phosphorus sources can be controlled with time, thereby controlling the length of the knot-like portions. Alternatively, the number of the knot-like portions can be controlled by controlling the number of changes in the supply rate of the carbon and phosphorus sources. In addition, whether the graphitic shells are formed on the surface of the apatite cores can be controlled by switching on or off the supply of the carbon source-containing reactant gas.

In yet another aspect, the present invention provides heterogeneous nanowires synthesized by the above method, which are composed of graphitic shells and apatite cores and have a thickness which changes in the thickness of the nanowires along the axial direction of the nanowires thereof. The heterogeneous nanowires may be used as biomaterials, nanomaterials, or nano/bio composite materials.

BRIEF DESCRIPTION OF THE DRAWINGS

The patent or application file contains at least one drawing executed in color. Copies of this patent or patent application publication with color drawings will be provided by the Office upon request and payment of the necessary fee.

The above and other objects, features and advantages of the present invention will be more clearly understood from the following detailed description taken in conjunction with the accompanying drawing, in which.

DETAILED DESCRIPTION OF THE INVENTION

Hereinafter, heterogeneous nanowires composed of graphitic shells and apatite cores according to the present invention and synthesis methods thereof will be described in detail with reference to the accompanying drawing.

Figure 1:
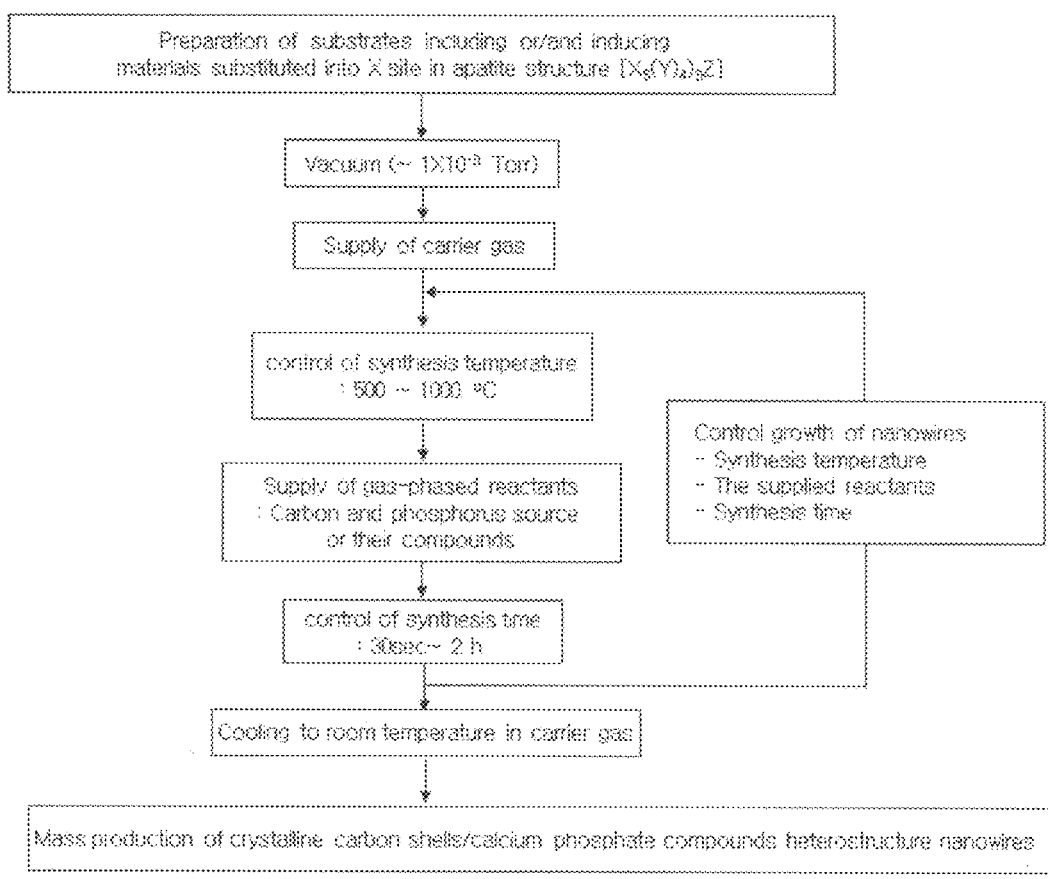
FIG. 1 is a flowchart showing a method for synthesizing single-crystal nanowires sheathed in graphitic shells according to the present invention.

FIG. 1 is a flowchart showing a method for synthesizing single-crystal nanowires sheathed in graphitic shells according to the present invention.

The inventive method for synthesizing single-crystal apatite nanowires comprising an apatite core sheathed in a graphitic shell comprises the steps of: i) introducing into a reactor either a material containing an element corresponding to X of $X_5(YO_4)_3(Z)$, which is a chemical formula for apatite, or a substrate containing the material; ii) maintaining the inside of the reactor in a vacuum and supplying a carrier gas to the reactor; iii) increasing the temperature of the reactor to synthesis temperature; iv) supplying reactant gases containing carbon and phosphorus sources to the reactor and allowing the reactant gases to react with the material or substrate, introduced into the reactor in step i); and v) cooling the reactor to room temperature in a carrier gas atmosphere.

In the method of the present invention, the element corresponding to X of the chemical formula of apatite may be Ca, K, Na, Sr, Ba, Mg, Pb, Cb or Zn. For example, if the element is calcium, the material containing the element is preferably a material which contains calcium or calcium oxide or can induce calcium or calcium. Examples of a biomaterial containing calcium include henequen and kenaf, which are woody biomasses, red algae and brown seaweed. Further, the shape of the substrate may be selected from mesh, foams, spheres, fibers, tubes, plates, thin films, powders, and nanoparticles. In one embodiment of the present invention, the substrate may be glass fiber or glass powder.

In addition, the substrate is preferably mounted in the reactor using an assistant material, such as a crucible or flat panel made of alumina or quartz which is stable to the reactant gases at a temperature ranging from room temperature to 1000° C.

Furthermore, in the step of controlling the internal atmosphere of the reactor before synthesis by a vacuum pump and by supply of a carrier gas, the internal pressure of the reactor is reduced to a vacuum of $1 \times 10^{-3}$ Torr by means of a vacuum pump in order to remove the remaining gas from the reactor. Then, the carrier gas is supplied to the reactor maintained in a vacuum. The carrier gas may be any one of argon, helium and nitrogen.

In addition, in the step of elevating the temperature of the reactor to synthesis temperature, the temperature of the reactor is preferably controlled in the range of 500 to 1000° C. while the carrier gas is supplied thereto. As the temperature of the reactor reaches to a desired temperature within the above range, reactant gases containing either a carbon source or a phosphorous source or derivatives thereof are supplied to the reactor.

Moreover, the carbon source-containing reactant gas that is supplied to the reactor controlled to the above temperature preferably includes a hydrocarbon gas such as acetylene, ethylene, ethane, propane or methane, and the phosphorus source-containing reactant gas preferably includes a phosphine gas.

Herein, the phosphine gas is one example of a reactant gas that contains phosphorus (P) among P, As, V and S, which are elements corresponding to Y in the apatite structure.

Also, the carbon source-containing reactant gas is supplied in order to form graphitic shells.

The reactant gases can react with each other during the synthesis process to induce new gaseous carbon-phosphorus organic compounds. If the carbon-phosphorus organic compounds are prepared in liquid form, they are preferably evaporated by heating or atomized by ultrasonic atomization, and then supplied to the reactor.

The supplied gaseous carbon source and phosphorus source can generate various gases in the above-specified reaction temperature range. Among these gaseous derivatives, the carbon-phosphorus organic compounds play a very important role in the nucleation and oriented growth of apatite crystals. Typical gaseous carbon-phosphorus organic compounds confirmed in the present invention phosphorine ($C_5H_5P$) and phosphinoline: ($C_9H_7P$).

The gaseous carbon-phosphorus organic compounds react with a calcium source material to form amorphous calcium phosphate nanoparticles which are then subjected to a nucleation and crystallization process with the passage of time, thereby forming crystalline apatite.

Herein, if the introduced substrate is a calcium-based material, amorphous calcium phosphate nanoparticles start to be formed on the surface of the substrate as amorphous calcium phosphate compounds are supplied. In this process, phosphorus molecules thermally decomposed from phosphine at synthesis temperature react with the oxygen of the substrate to form phosphates which then react with calcium, thereby forming amorphous calcium phosphate compounds. In addition, because the gaseous carbon-phosphate organic compounds resulting from the reaction between the carbon and the phosphorus source-containing reactant gas can induce the strong bonding between the calcium and the phosphate, they can also promote the formation of amorphous calcium phosphate nanoparticles. Then, the amorphous calcium phosphate nanoparticles undergo a nucleation and crystallization process, and the gaseous carbon-phosphorus organic compounds also play a role in promoting this nucleation and crystallization process and function to induce the apatite crystal to be oriented in one plane that is the (001) plane. When the phosphorus and calcium-containing gaseous species are continuously supplied, one-dimensional apatite nanowires oriented in the (001) plane grow, while graphitic shells are formed around the radial surface of the apatite nanowires under continuous supply of the carbon source-containing reactant gas. The graphitic shells formed around the apatite nanowires function to block the phosphorus and calcium-containing gaseous species from being supplied to the radial surface of the nanowires, thereby preventing the lateral growth of the nanowires. In addition, the formed graphitic shells function to promote the growth of the nanowire in the axial direction. As a result, the inventive apatite nanowires sheathed in graphitic shells can be formed by a CVD-based vapor-solid (VS) growth mechanism. In this formation process, the gaseous carbon-phosphorus organic compounds can play a very important role in the formation and oriented growth of apatite crystals.

Figure 15:
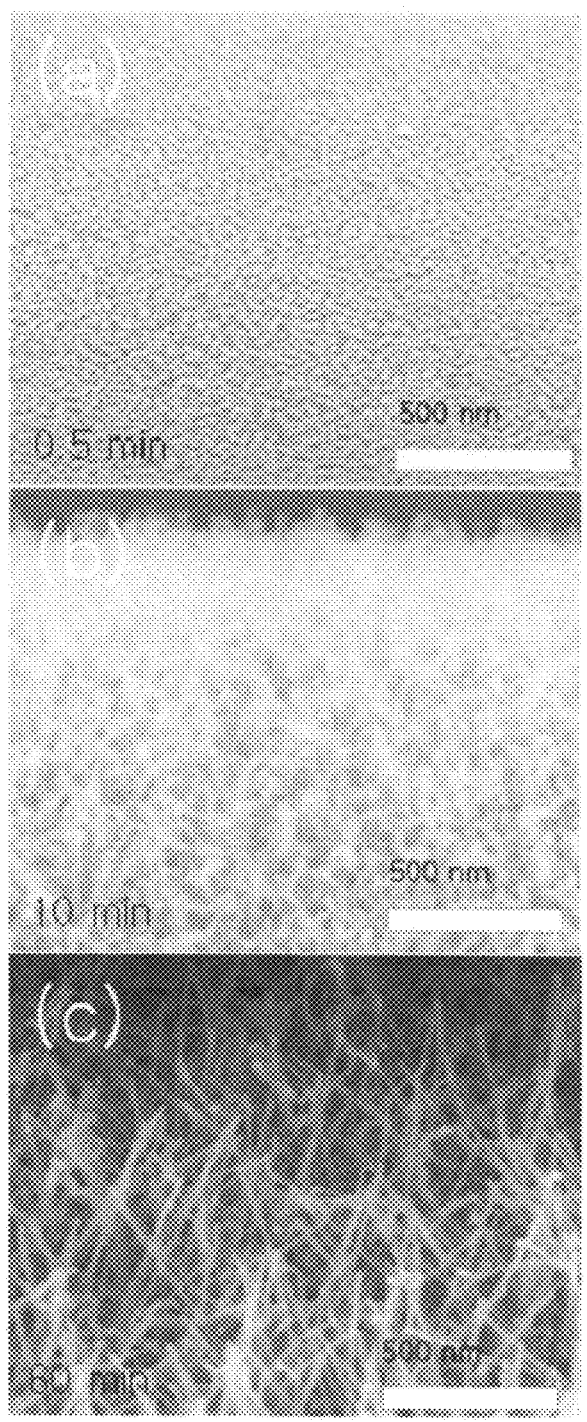
FIG. 15 shows the results of observation of the inventive single-crystal nanowires sheathed in graphitic shells as a function of synthesis time.
Figure 16:
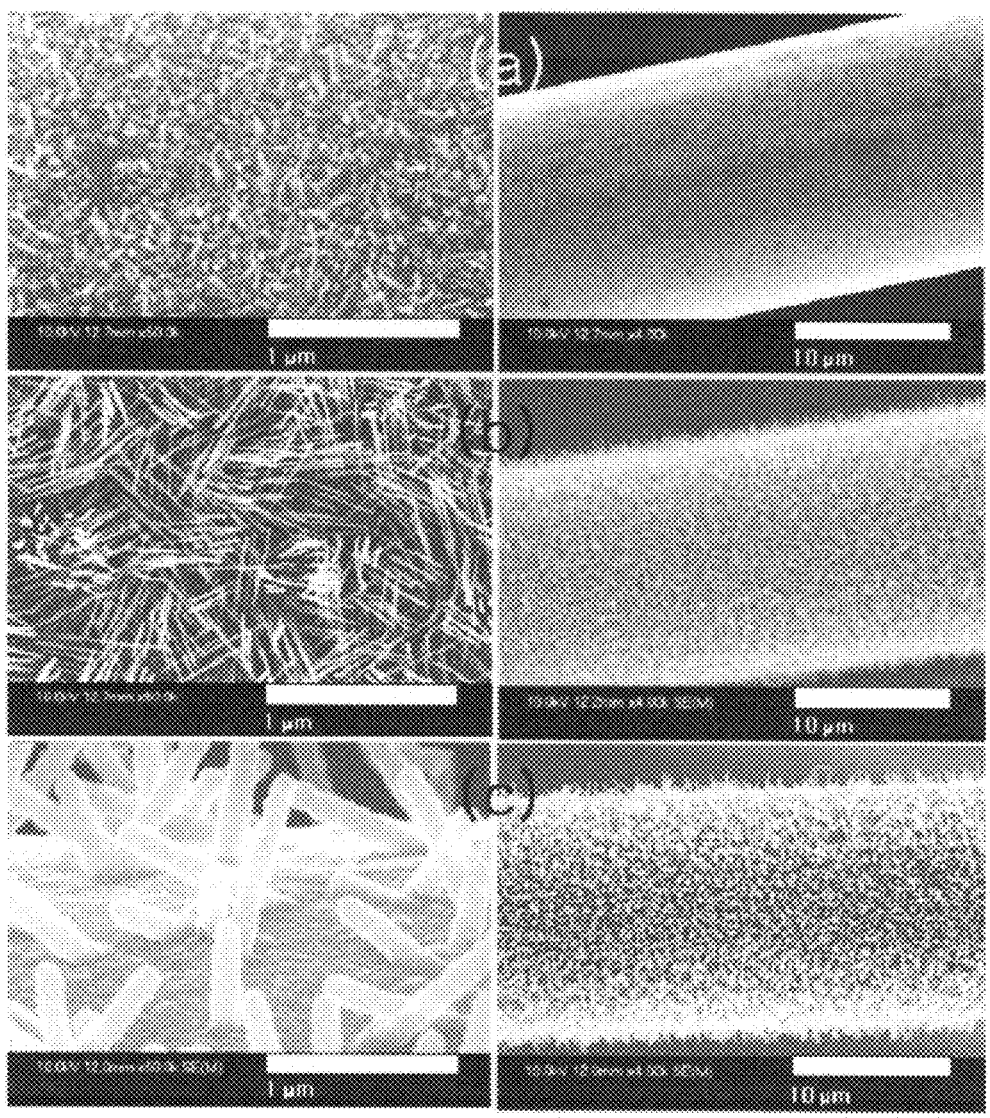
FIG. 16 shows the results of observation of the inventive single-crystal nanowires sheathed in graphitic shells as a function of synthesis temperature.

The synthesis of such heterogeneous nanowires comprising graphitic shells and apatite cores is continuously performed during the synthesis process. If the conditions of synthesis are controlled, heterogeneous nanowires, which comprise graphitic shells and apatite cores and have the shapes controlled in the axial direction (growth direction) as shown in FIGS. 15 and 16 below, can be obtained.

Particularly, it was confirmed in the present invention that the shape of heterogeneous nanowires can be freely controlled by controlling the reaction temperature for synthesis, the reaction time, and the concentration of the carbon source or phosphorus source in the reactant gases being supplied. The heterogeneous nanowires synthesized in this manner are composed of graphitic shells and apatite cores and are characterized in that knot-like structures are formed.

Herein, the length of the knot-like portions can be controlled by controlling the supply rate of the carbon and phosphorus sources with time. Alternatively, the number of the knot-like portions can be controlled by controlling the number of changes in the supply rate of the carbon and phosphorus sources. In addition, whether the graphitic shells are formed on the surface of the apatite cores can be controlled by switching on or off the supply of the carbon source-containing reactant gas.

After the reactant gases are supplied as described above, the reaction time for synthesis is controlled. In this step, the reaction time is controlled within the range of 30 seconds to 2 hours, and the synthesis time can have a direct influence on the growth of length of heterogeneous nanowires.

After completion of the synthesis, the reactor is cooled in an atmosphere of a carrier gas alone, and finally, heterogeneous nanowires composed of graphitic shells and apatite cores can be obtained.

Meanwhile, the present invention provides single-crystal apatite nanowires sheathed in graphitic shells, synthesized by the above-described method. In a preferred embodiment, apatite comprises 99-100% of the inner cavity of the graphitic shells, the nanowires have a diameter of 5 nm to 20 nm and a length of 100 nm to 5 μm, and the graphitic shells have a thickness of 0.34-2 nm. The heterogeneous nanowires may be used as biomaterials, nanomaterials, or nano/bio composite materials.

The inventive method for synthesizing heterogeneous nanowires composed of graphitic shells and apatite cores have a very important significance in that it is very simple, and at the same time, makes it possible to achieve the simultaneous synthesis of graphitic shells and apatite cores, which has been considered difficult in the prior art. In addition, the method of the present invention is a novel method which is highly reproducible and can also be applied to a mass production process.

Hereinafter, examples of heterogeneous nanowires composed of graphitic shells and apatite cores according to the present invention will be described. It is to be understood, however, that these examples are not intended to limit the scope of the present invention and may be modified in various forms without departing from the scope of the present invention.

Example 1

Figure 2:
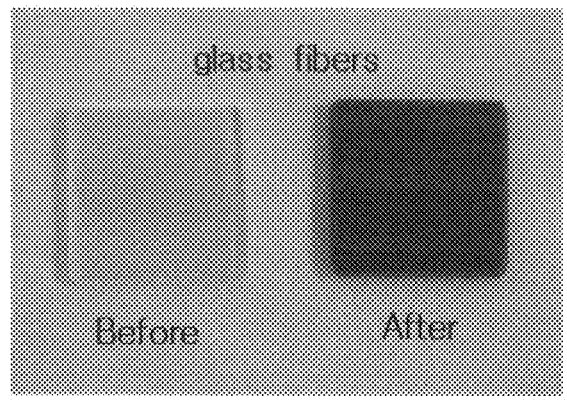
FIG. 2 shows photographs before and after synthesis of the inventive single-crystal apatite nanowires sheathed in graphitic shells, grown on glass fiber.

Results of Observation Before and after Synthesis of Single-Crystal Apatite Nanowires Sheathed in Graphitic Shells FIG. 2 shows photographs before and after synthesis of the inventive single-crystal apatite nanowires sheathed in graphitic shells, grown on glass fiber. Herein, the prepared calcium-containing material was glass fiber, and the glass fiber used was dispersed uniformly on a quartz plate to form a thin film. The formed glass fiber thin film was mounted in a reactor, and synthesis was performed using argon gas as a carrier gas at 750° C. The synthesis time was 1 hour, and acetylene and phosphine gas were used as reactant gases.

Example 2

Figure 3:
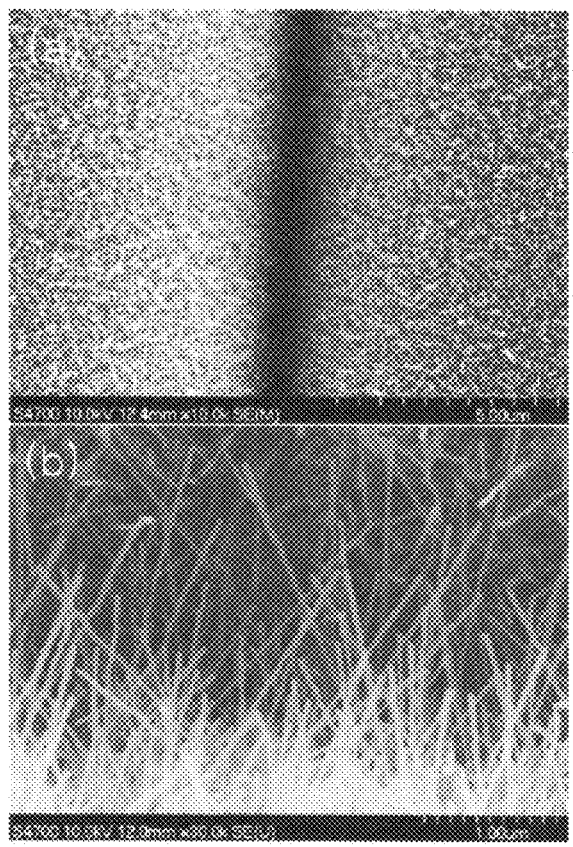
FIG. 3 shows a scanning electron microscopy (SEM) image of the inventive single-crystal apatite nanowires sheathed in graphitic shells, grown on glass fiber.

SEM Image of Single-Crystal Apatite Nanowires Sheathed in Graphitic Shells, Grown on Glass Fiber FIG. 3 shows an SEM (scanning electron microscopy) of the inventive single-crystal apatite nanowires sheathed in graphitic shells, growth on glass fiber. As can be seen therein, the synthesized heterogeneous nanowires were distributed very uniformly on the glass fiber. These nanowires had a length of about 1-2 μm and a diameter of 20 nm or less. The synthesized heterogeneous nanowires contained tooth-to-tooth contacts between the glass fibers, suggesting that the nanowires were grown very densely.

Example 3

Figure 4:
FIG. 4 shows a SEM image of the inventive single-crystal apatite nanowires sheathed in graphitic shells, grown on glass powder.

SEM Image of Single-Crystal Apatite Nanowires Sheathed in Graphitic Shells, Grown Glass Powder FIG. 4 shows an SEM image of the inventive single-crystal apatite nanowires sheathed in graphitic shells, growth on glass powder. As shown therein, the heterogeneous nanowires were also distributed uniformly throughout the surface of glass powder having a particle size of about 5 μm. The size of the produced heterogeneous nanowires appeared to be similar to that of the nanowires grown on glass fiber, but these nanowires appeared to grow to a final length of 5 μm. Such results confirmed that the shape of heterogeneous nanowires growing on a calcium-containing material is not significantly influenced by the size and shape of the calcium-containing material.

Example 4

Results of XRD of Single-Crystal Apatite Nanowires Sheathed in Graphitic Shells

Figure 5:
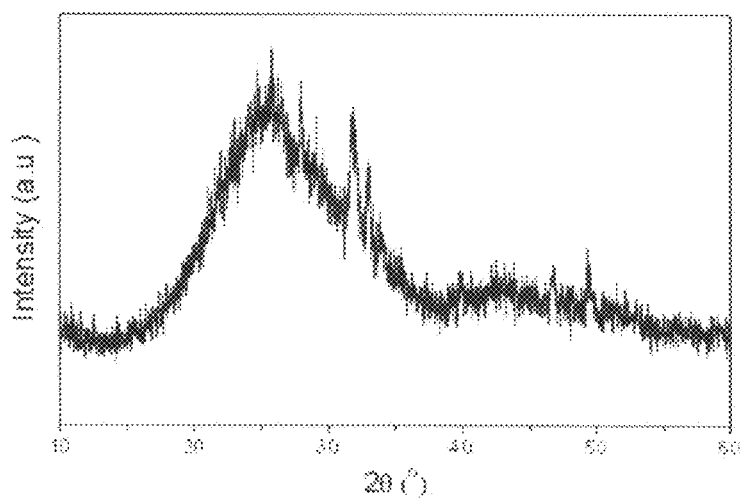
FIG. 5 shows the results of X-ray diffraction (XRD) of the inventive single-crystal nanowires sheathed in graphitic shells.

FIG. 5 shows the results of XRD of the inventive single-crystal apatite nanowires sheathed in graphitic shells. As can be seen therein, in the 2θ region between 15° and 35°, amorphous patterns of amorphous glass appear. In this region, the major peaks of apatite are also observed. At around 2θ=31.8°, a strong peak corresponding to the (211) plane of apatite is observed. In addition, the peaks corresponding the (300), (112) and (002) planes are strongly observed at around 2θ=32.9°, 32.2° and 25.9°.

Example 5

Figure 6:
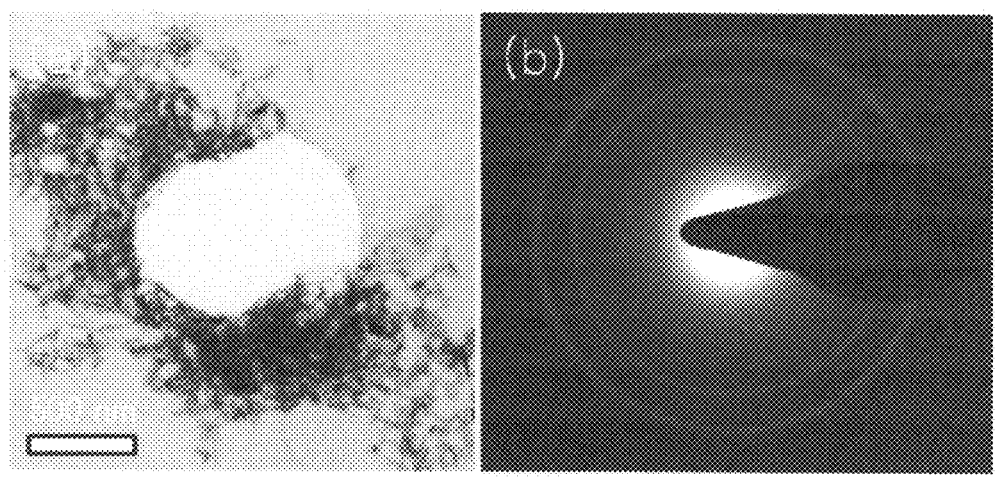
FIG. 6 shows transmission electron microscopy (TEM) image and selected area electron diffraction (SAED) images of the inventive single-crystal nanowires sheathed in graphitic shells.

TEM and SAED Patterns of Single-Crystal Apatite Nanowires Sheathed in Graphitic Shells FIG. 6 shows the TEM image and SAED patterns of the inventive single-crystal apatite nanowires sheathed in graphitic shells. Nanowires dispersed on the TEM grid as shown in the TEM image (FIG. 6(a)) is shown in FIG. 6(b). Although the nanowires are single crystals, the diffraction patterns in the area in which these nanowires are randomly dispersed appear like polycrystalline structures, and such results are indicated by white circular bands in FIG. 6(b). The distance between the white circular bands was calculated, and as a result, the distance between the planes was exactly consistent with the results calculated for the XRD diffraction patterns shown in Example 4.

Example 6

TEM Image of Single-Crystal Apatite Nanowires Sheathed in Graphitic Shells

Figure 7:
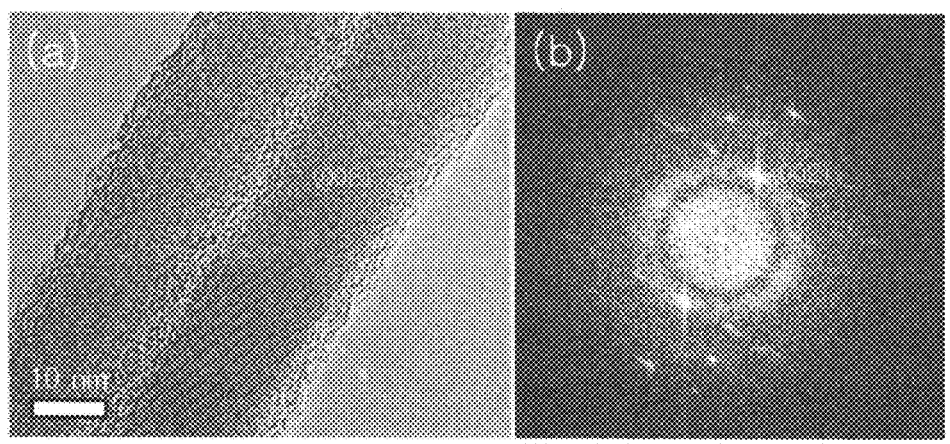
FIG. 7 shows a TEM image of the inventive single-crystal nanowires sheathed in graphitic shells.

FIG. 7 shows a TEM image of the inventive single-crystal apatite nanowires sheathed in graphitic shells. FIG. 7(a) shows the crystal image of the produced heterogeneous nanowires. As shown therein, the heterogeneous nanowires have a structure in which the nanowire core is sheathed in a shell. The shell was observed to have a very thin thickness of less than 2 nm, and the nanowire corresponding to the inner core had a diameter of about 15 nm and was single-crystalline. It was observed that the nanowire corresponding to the inner core was grown perpendicularly to the (002) plane of apatite, and this result is evident from the diffraction pattern of the image shown in FIG. 7(a).

Example 7

Figure 8:
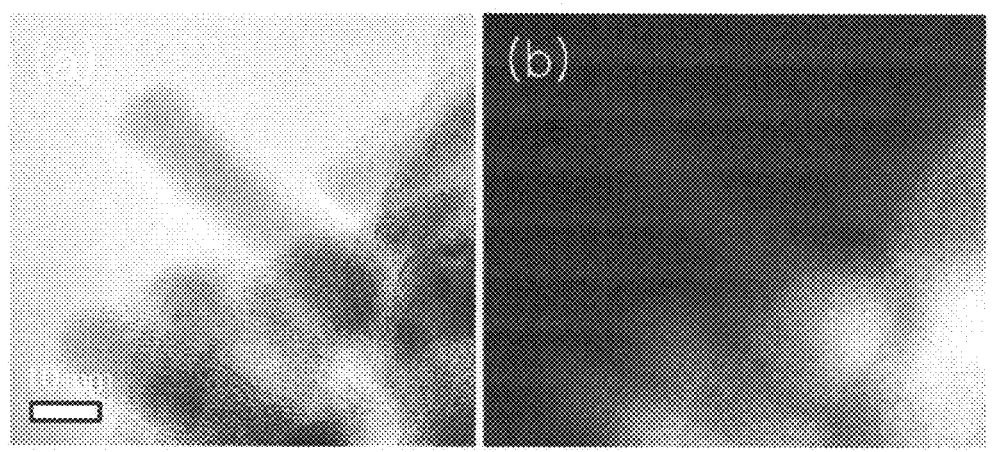
FIG. 8 shows TEM and scanning transmission electron microscopy (STEM) images of the inventive single-crystal nanowires sheathed in graphitic shells.

TEM and STEM Images of Single-Crystal Apatite Nanowires Sheathed in Graphitic Shells FIG. 8 shows TEM and STEM images of the inventive single-crystal apatite nanowires sheathed in graphitic shells. FIG. 8(a) shows an energy filtered (EF)-TEM image of the nanowires. As can be seen therein, the nanowire has a diameter of 15 nm or less and is sheathed in a thin shell. FIG. 8(b) shows an STEM image of the nanowires.

Example 8

Figure 9:
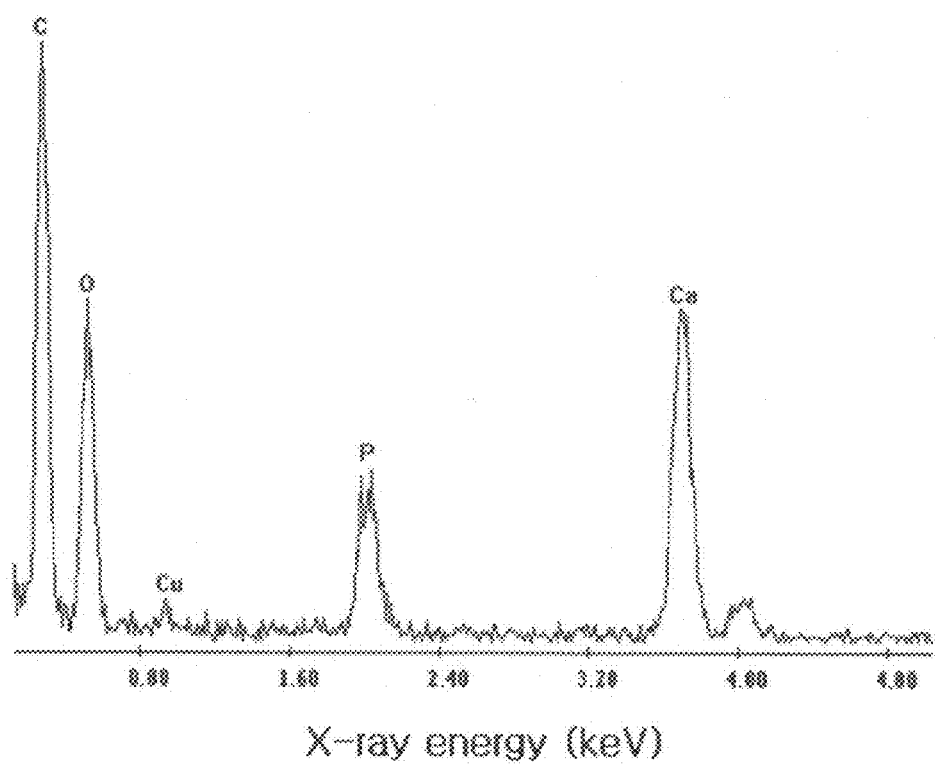
FIG. 9 shows the results of energy dispersive X-ray spectroscopy (EDX) of the inventive single-crystal nanowires sheathed in graphitic shells.

Results of EDX Analysis of Single-Crystal Apatite Nanowires Sheathed in Graphitic Shells FIG. 9 shows the results of EXD analysis of the inventive single-crystal apatite nanowires sheathed in graphitic shells.

As can be seen therein, calcium, phosphorus, oxygen and carbon were detected in the nanowire. Herein, the detected copper is attributable to the TEM grid. In addition, calcium, phosphorus and oxygen are the fundamental components of apatite, and carbon was detected in the grid and the shell of the heterogeneous nanowires.

Example 9

Figure 10:
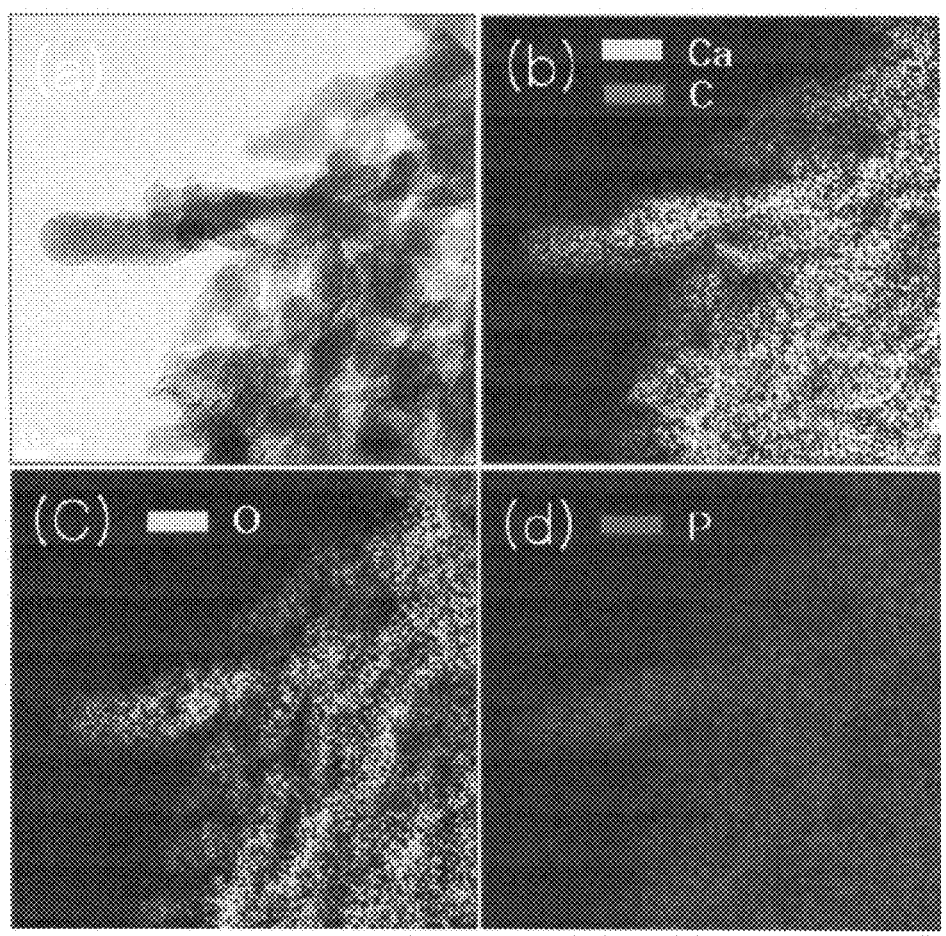
FIG. 10 shows the results of electron energy loss spectroscopy (EELS) mapping of the inventive single-crystal nanowires sheathed in graphitic shells.

Results of EELS Analysis of Single-Crystal Apatite Nanowires Sheathed in Graphitic Shells FIG. 10 shows the results of EELS mapping analysis of the inventive single-crystal apatite nanowires sheathed in graphitic shells. In the results of EELS analysis of heterogeneous nanowires as shown in the EF-TEM image of FIG. 10(a), calcium, phosphorus and oxygen were detected in the inner core, and carbon was detected in the outer shell. Such results are completely consistent with the results of TEM and EDX observed in the above examples, suggesting that the heterogeneous nanowires synthesized according to the present invention are composed of graphitic shells and apatite cores.

Example 10

Results of XPS of Single-Crystal Apatite Nanowires Sheathed in Graphitic Shells

Figure 11:
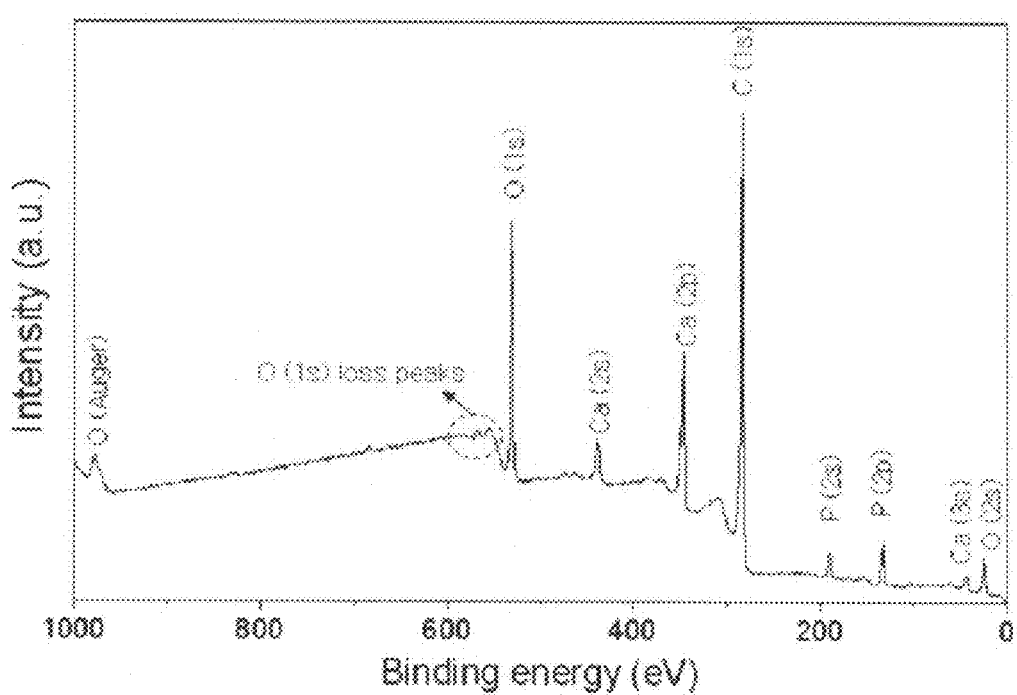
FIG. 11 shows the results of X-ray photoelectron spectroscopy (XPS) of the inventive single-crystal nanowires sheathed in graphitic shells.

FIG. 11 shows the results of XPS of the inventive single-crystal apatite nanowires sheathed in graphitic shells. As can be seen therein, the C (1S) peak corresponding to carbon is the strongest peak. In addition, Ca (2P), P (2p), O (1s) peaks appear. XPS is a system for analyzing the surface properties of a material, and the results of this example indicate that the major component of the shell of the heterogeneous nanowires is carbon and that the major components of the inner core are calcium, phosphorus and oxygen. Also, the loss peaks of O (1s) can be observed in typical calcium phosphate compounds and related materials and show a tendency similar to that observable in apatite.

Example 11

Figure 12:
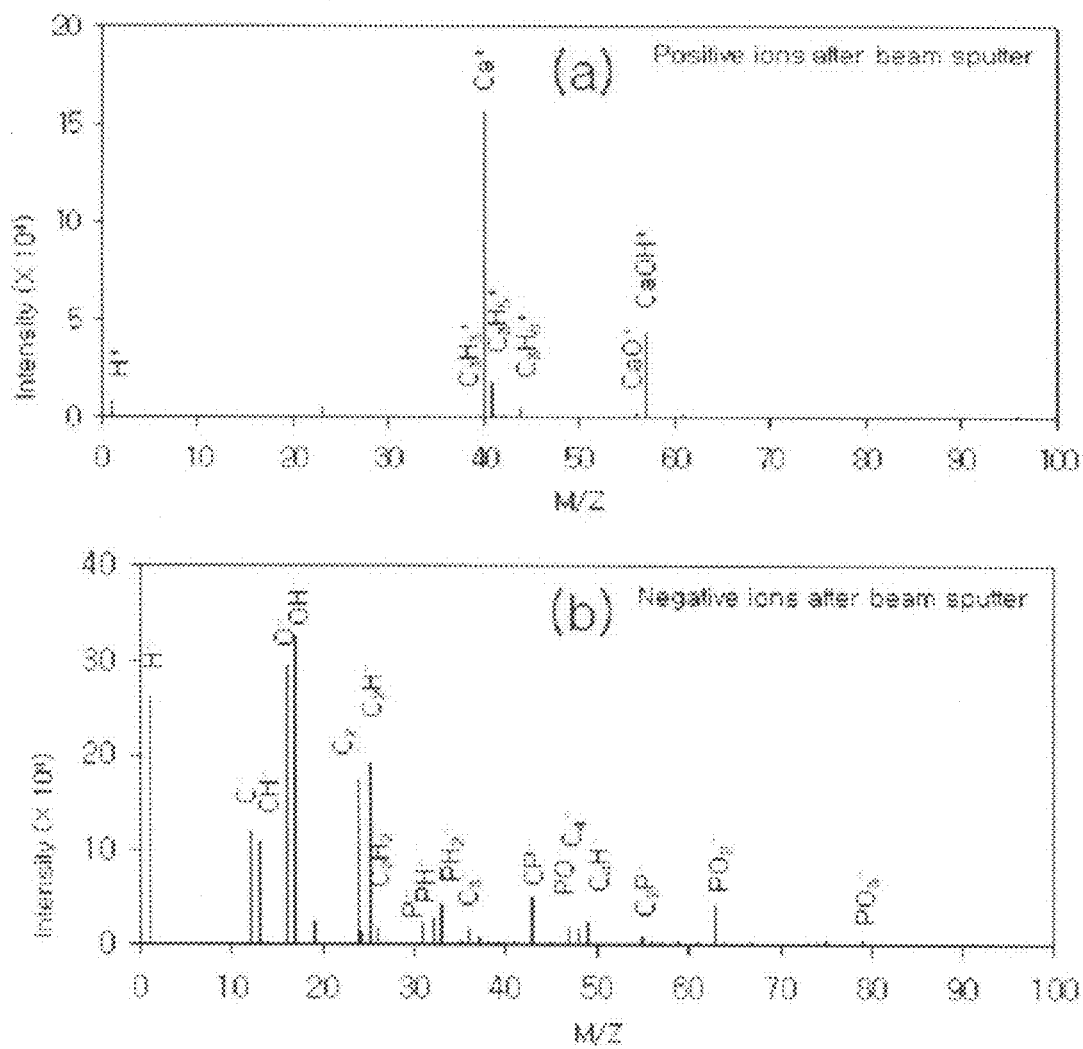
FIG. 12 shows the results of time-of-flight secondary ion mass spectroscopy (TOF-SIMS) of the inventive single-crystal nanowires sheathed in graphitic shells.

Results of TOF-SIMPS of Single-Crystal Apatite Nanowires Sheathed in Graphitic Shells FIG. 12 shows the results of TOF-SIMS of the inventive single-crystal apatite nanowires sheathed in graphitic shells. In this Example, the surface of the sample was treated with bismuth ions for a short time. Measurement results for the positive and negative ions of the sample surface are shown in FIGS. 12(a) and (b), respectively.

For the positive ions, the results related to $Ca^+$, $CaO^+$, $Ca(OH)^+$ and $C_xH_y$ were measured. It is believed that calcium cations were detected in the core of the heterogeneous nanowires and that hydrocarbon cations were detected in the graphitic shell. In the sample whose surface was not treated with ions, the peaks corresponding to hydrocarbon cations were more strongly detected.

For the negative ions, the peaks of $PO_x^-$, $C_xP_y$, $C_z^-$, $O^-$ and $OH^-$ were mainly detected. It is believed that phosphate anions ($PO_x^-$) and oxygen and hydroxide anions were detected in the apatite core and that carbon-related anions were detected in the graphitic shell. In the sample whose surface was not treated with ions, the peaks corresponding to hydrocarbon anions were more strongly detected. Particularly, it was observed that, after the surface of the heterogeneous nanowires was treated with ions, the amount of hydroxide anions detected increased.

Example 12

Figure 13:
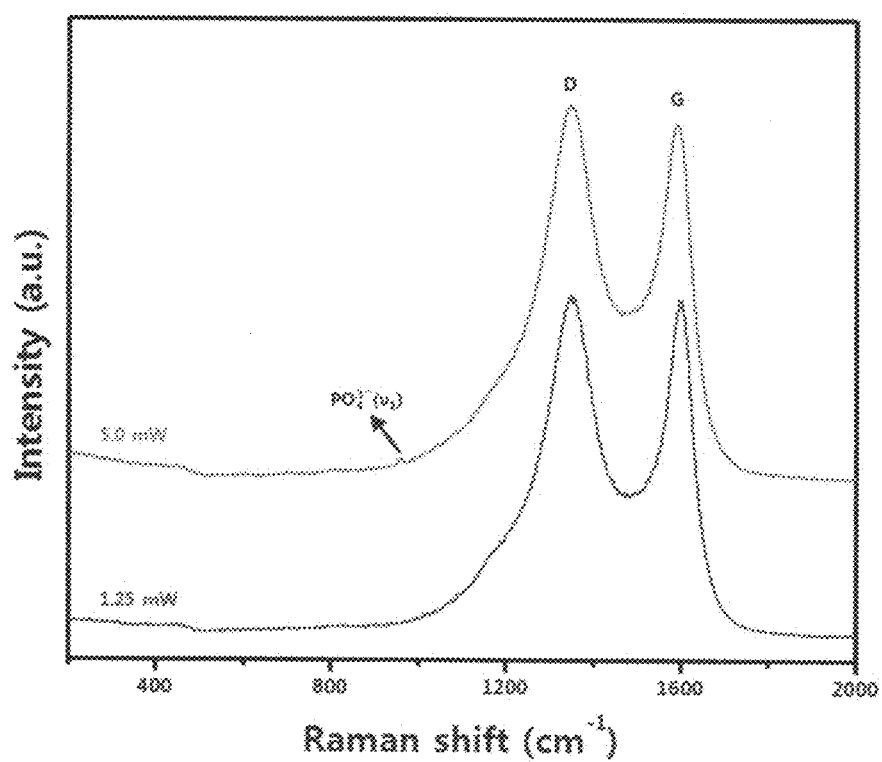
FIG. 13 shows the results of Raman spectroscopy of the inventive single-crystal nanowires sheathed in graphitic shells.

Results of Raman Spectroscopy of Single-Crystal Apatite Nanowires Sheathed in Graphitic Shells FIG. 13 shows the results of Raman spectroscopy of the inventive single-crystal apatite nanowires sheathed in graphitic shells. The results in FIG. 13 were measured at 514 nm laser source. The peaks appearing at around 1350 and 1580 $cm^{-1}$ of the spectrum are the D and G peaks of carbon detected in the graphitic shells. The peak measured between 900 and 1000 $cm^{-1}$ at an energy intensity of 5 mW appears to correspond to a phosphate-related band detected in the apatite core.

Example 13

Figure 14:
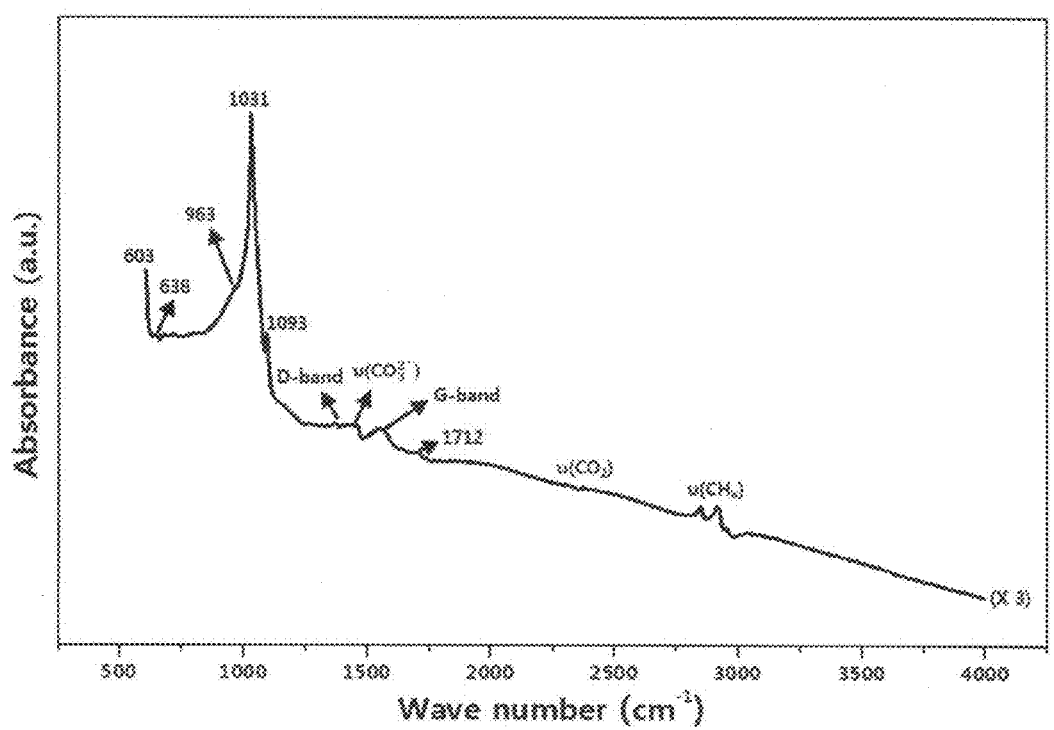
FIG. 14 shows the results of Fourier transform infrared spectroscopy (FT-IR) of the inventive single-crystal nanowires sheathed in graphitic shells.

Results of IR Spectroscopy of Single-Crystal Apatite Nanowires Sheathed in Graphitic Shells FIG. 14 shows the results of FT-IR spectroscopy of the inventive single-crystal apatite nanowires sheathed in graphitic shells. Peaks which are typically observed in apatite appear at around 600, 960, 1030 and 1090 $cm^{-1}$. In addition, an IR peak corresponding to multiwall carbon nanotubes was observed at around 1570 $cm^{-1}$. Also, at around 3570 $cm^{-1}$, a peak corresponding to OH was very weakly observed. The results of this Example together with the results of Raman spectroscopy confirm that the heterogeneous nanowires of the present invention are composed of graphitic shells and apatite cores.

Example 14

Results of Observation of Single-Crystal Apatite Nanowires Sheathed in Graphitic Shells as a Function of Synthesis Time FIG. 15 shows the results of observation of the inventive single-crystal apatite nanowires sheathed in graphitic shells as a function of synthesis time. FIG. 15(a) shows an SEM image obtained 30 seconds after the start of synthesis and indicates nanoparticles of very small size on the substrate surface. It was observed that these particles were transformed into one-dimensional nanostructures gradually with the passage of time and had a nanorod shape after 10 minutes (FIG. 15(b)). 60 minutes after the start of synthesis (FIG. 15(c)), the produced nanostructures had a complete nanowire shape.

Example 15

Results of Observation of Single-Crystal Apatite Nanowires Sheathed in Graphitic Shells as a Function of Synthesis Temperature FIG. 16 shows the results of observation of the inventive single-crystal apatite nanowires sheathed in graphitic shells as a function of synthesis temperature. FIGS. 16(a), (b) and (c) show SEM images obtained at synthesis temperatures of 650, 750 and 850° C., respectively. In the SEM image at 650° C., the nanostructures formed on the substrate surface appear like short irregular nanorods. At a synthesis temperature of 750° C., it is observed that very thin mature nanowires cover the substrate surface in a very uniform and dense manner. At a synthesis temperature of 850° C., it is observed that the diameter of the formed nanowires significantly increases. In addition, the results of additional TEM analysis indicated that the thickness of the graphitic shells rapidly increased with an increase in synthesis temperature and this tendency was more remarkable at synthesis temperatures higher than 750° C.

Example 16

Figure 17:
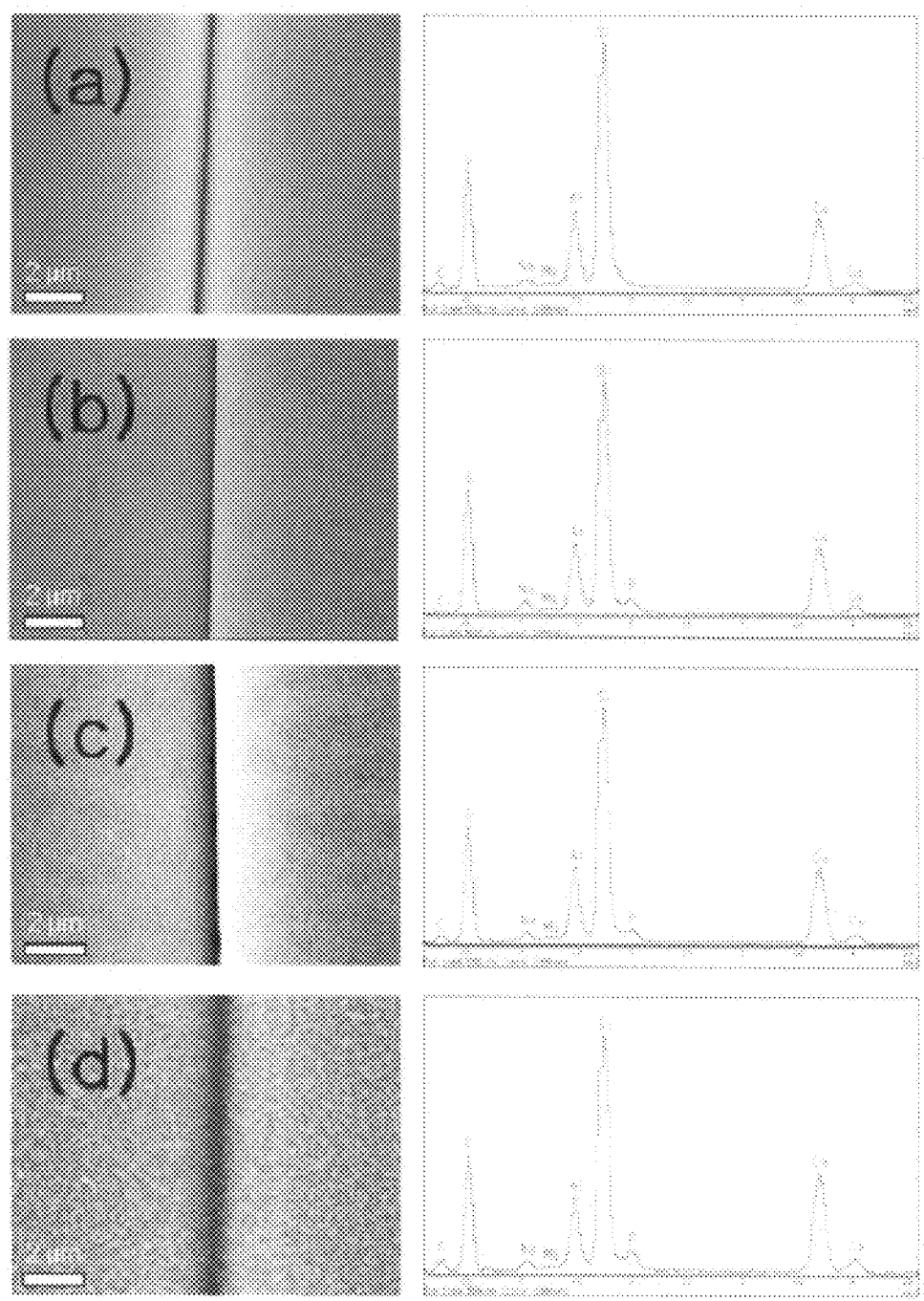
FIG. 17 shows the results of observation of the inventive single-crystal nanowires sheathed in graphitic shells according as a function of the conditions of reactant gases.

Results of Observation of Single-Crystal Apatite Nanowires Sheathed in Graphitic Shells as a Function of the Conditions of Synthesis Temperature FIG. 17 shows the results of observation of the inventive single-crystal apatite nanowires sheathed in graphitic shells as a function of the conditions of synthesis gases. FIG. 17(a) shows the results obtained when a carbon source alone was supplied as a reactant gas. As can be seen therein, the substrate surface remained relatively clean. The results of analysis for the components of the surface indicated that carbon in addition to the components of the substrate was detected.

FIG. 17(b) shows the results obtained when a phosphorus source alone was supplied as a reactant gas. As can be seen therein, small protrusions were formed on the substrate surface. In the results of component analysis, phosphorus in addition to the components of the substrate was detected and little or no carbon was detected. The results of additional TEM analysis indicated that the obtained nano-protrusions mostly showed the properties of amorphous calcium phosphate compounds.

FIG. 17(c) shows the results obtained when a carbon source alone was supplied to a product obtained by supplying a phosphorous source alone as a reactant gas. The surface shape of the substrate appears to be similar to that in FIG. 17(b). In the results of component analysis, phosphorous and carbon components in addition to the components of the substrate were detected. However, the structures formed on the surface still showed an nano-protrusion shape.

FIG. 17(d) shows the results obtained when a carbon source and a phosphorus source were simultaneously supplied as reactant gases. As can be seen therein, nanostructures formed on the surface all showed a nanowire shape. The results of additional TEM analysis indicated that the nanowires formed on the surface all have a single-crystal apatite structure.

Example 17

Figure 18:
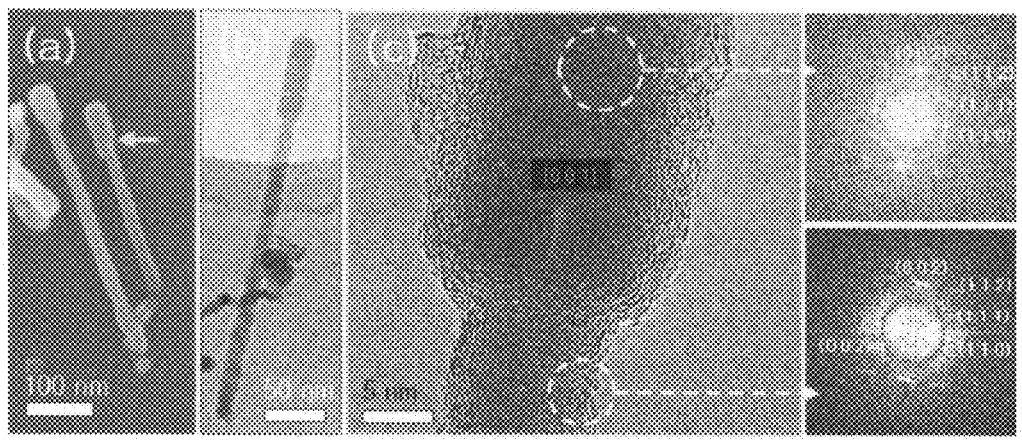
FIG. 18 shows the results of controlling the shape of the inventive single-crystal nanowires sheathed in graphitic shells by changing the supply rate of reactants once during synthesis of the nanowires.

Results of One-Stage Shape Control Performed During Synthesis of Single-Crystal Apatite Nanowires Sheathed in Graphitic Shells FIG. 18 shows the results of one-stage shape control performed during the synthesis of the inventive single-crystal apatite nanowires sheathed in graphitic shells. In this Example, the supply of carbon and phosphorous sources as reactant gases was changed once during the synthesis of heterogeneous nanowires. FIGS. 18(a) and (b) show SEM and TEM images of the products obtained by changing the supply once, respectively. The resulting heterogeneous nanowires all had a structure in which the end of each nanowire has one knot-like portion (head portion) having a diameter larger than that of the stem. The results of TEM analysis of this structure indicated that the stem and the head portion had the same apatite structure and were grown in the same direction (FIG. 18(c)).

Example 18

Figure 19:
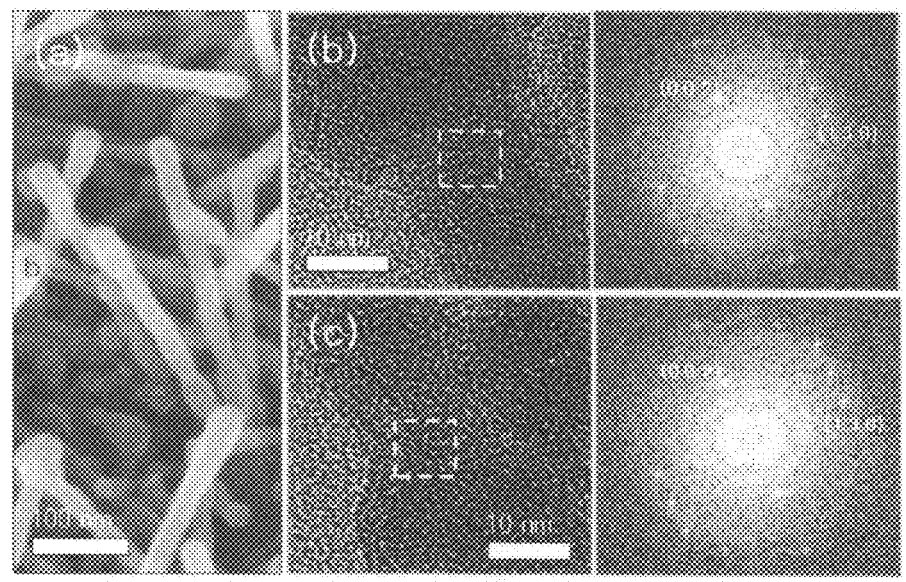
FIG. 19 shows the results of controlling the shape of the inventive single-crystal nanowires sheathed in graphitic shells by changing the supply rate of reactants twice during synthesis of the nanowires.

Results of Two-Stage Shape Control Performed During Synthesis of Single-Crystal Apatite Nanowires Sheathed in Graphitic Shells FIG. 19 shows the results of two-stage shape control performed during the synthesis of the inventive single-crystal apatite nanowires sheathed in graphitic shells. In this Example, the supply of carbon and phosphorous sources as reactant gases was changed twice during the synthesis of heterogeneous nanowires. The resulting heterogeneous nanowires all had two knot-like portions (head portions) formed along the growth direction of the nanowires. The diameter of the head portions was larger than that of the stem as in the case of FIG. 18. FIG. 19(a) shows an SEM image of the resulting products. TEM images of the portions indicated by two arrows in FIG. 19(a) are shown in FIGS. 19(b) and (c). The structure and growth direction of the two formed head portions were the same as those of the stem of the nanowires.

Example 19

Figure 20:
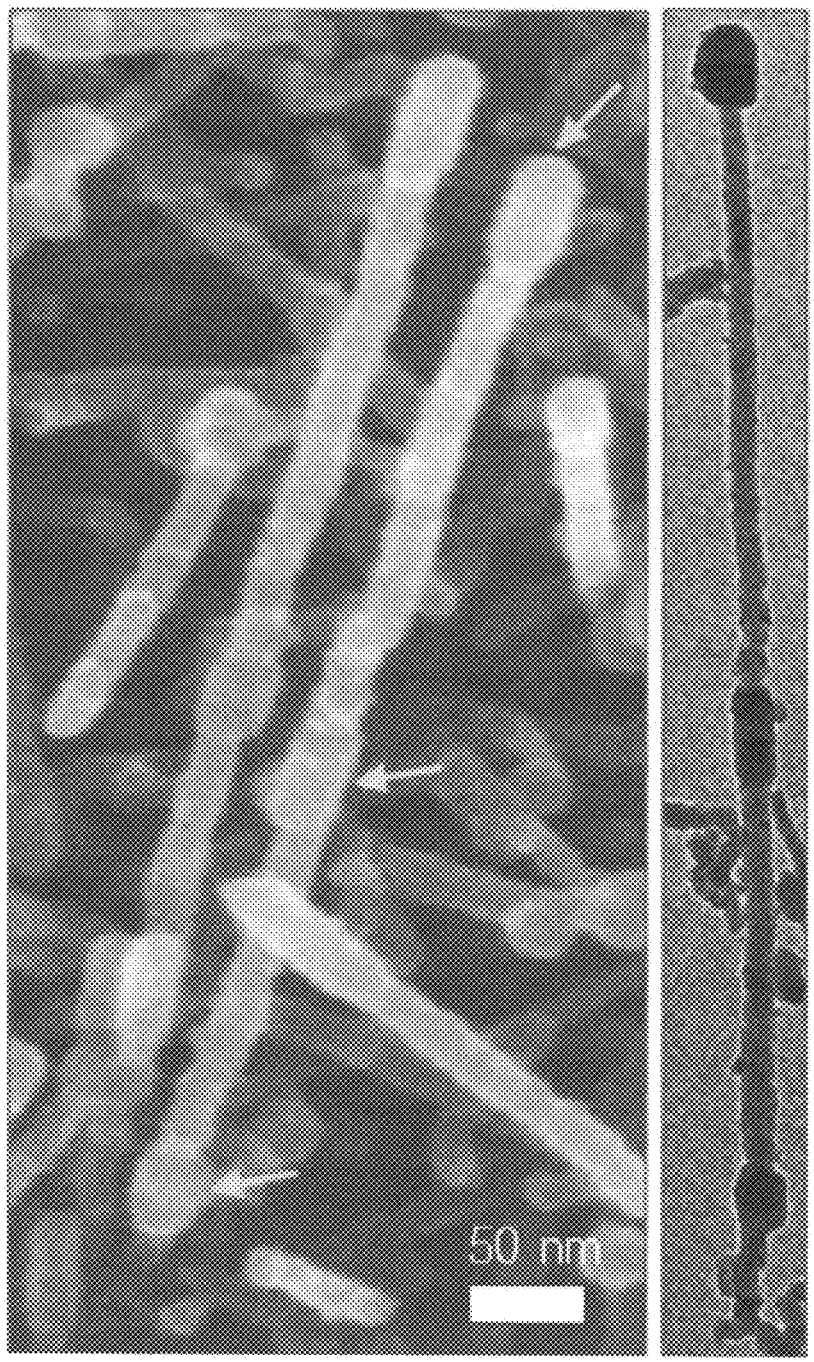
FIG. 20 shows the results of controlling the shape of the inventive single-crystal nanowires sheathed in graphitic shells by changing the supply rate of reactants three times during synthesis of the nanowires.

Results of Three-Stage Shape Control Performed During Synthesis of Single-Crystal Apatite Nanowires Sheathed in Graphitic Shells FIG. 20 shows the results of three-stage shape control performed during the synthesis of the inventive single-crystal apatite nanowires sheathed in graphitic shells. In this Example, the supply of carbon and phosphorous sources as reactant gases was changed three times during the synthesis of heterogeneous nanowires. The resulting heterogeneous nanowires all had three knot-like portions (head portions) formed along the growth direction of the nanowires. The diameter of the head portions was larger than that of the stem as in the case of FIGS. 17 and 18. TEM images of the portions indicated by three arrows, in FIG. 20(a) indicated that the structure and growth direction of the formed heads were the same as those of the stem of the nanowires.

Example 20

Figure 21:
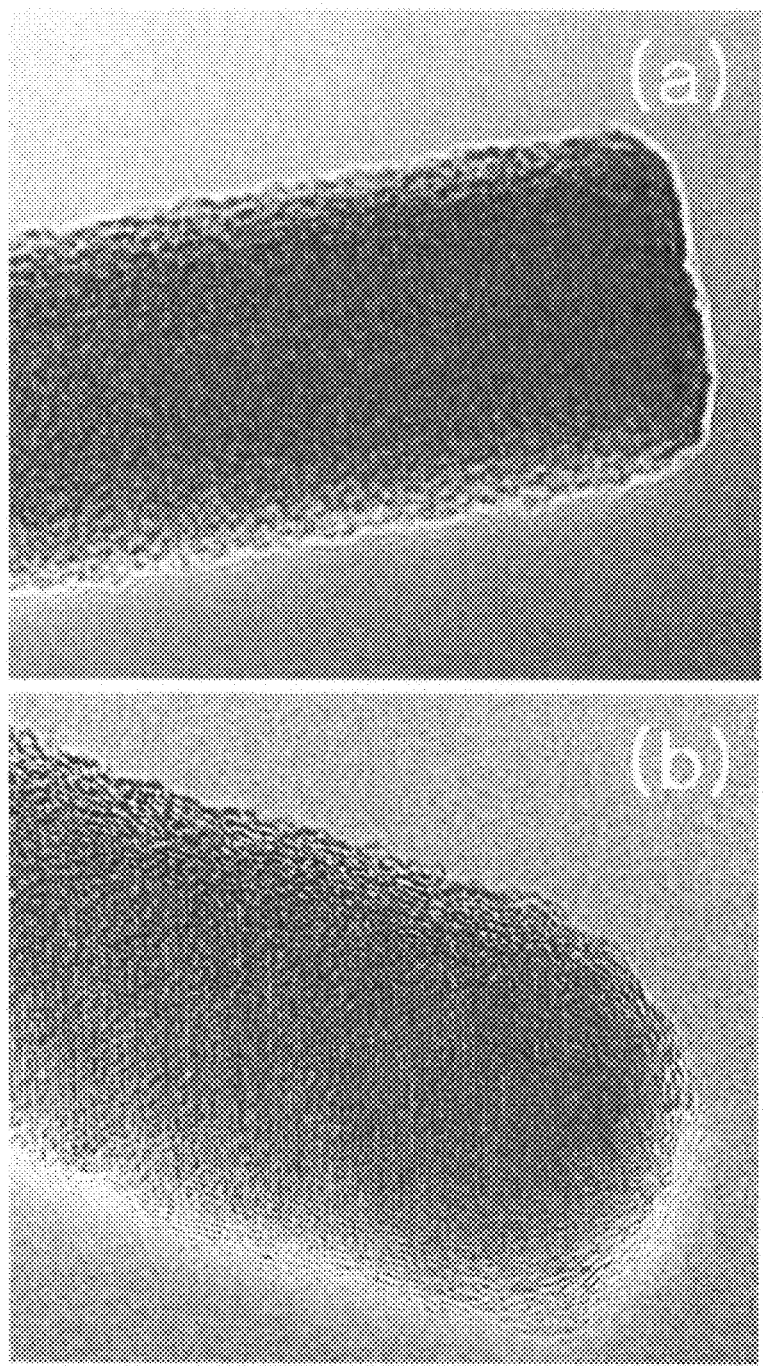
FIG. 21 shows the results of controlling the formation of graphitic shells in the inventive single-crystal nanowires sheathed in graphitic shells.

Results of Control of Formation of Crystalline Graphitic Shells During Synthesis of Single-Crystal Apatite Nanowires Sheathed in Graphitic Shells FIG. 21 shows the results of control of formation of graphitic shells during the synthesis of the inventive single-crystal apatite nanowires sheathed in graphitic shells. In FIG. 21(a), a carbon source and a phosphorous source were changed during the synthesis of heterogeneous nanowires such that no graphitic shell was formed on the surface of the resulting heterogeneous nanowires. However, when the sample shown in FIG. 21(a) was reacted with a carbon source, graphitic shells could be formed on the surface of the nanowire as shown in FIG. 21(b). Such results suggest that the formation of graphitic sells can be freely controlled during formation of the heterogeneous nanowires.

Example 21

Figure 22:
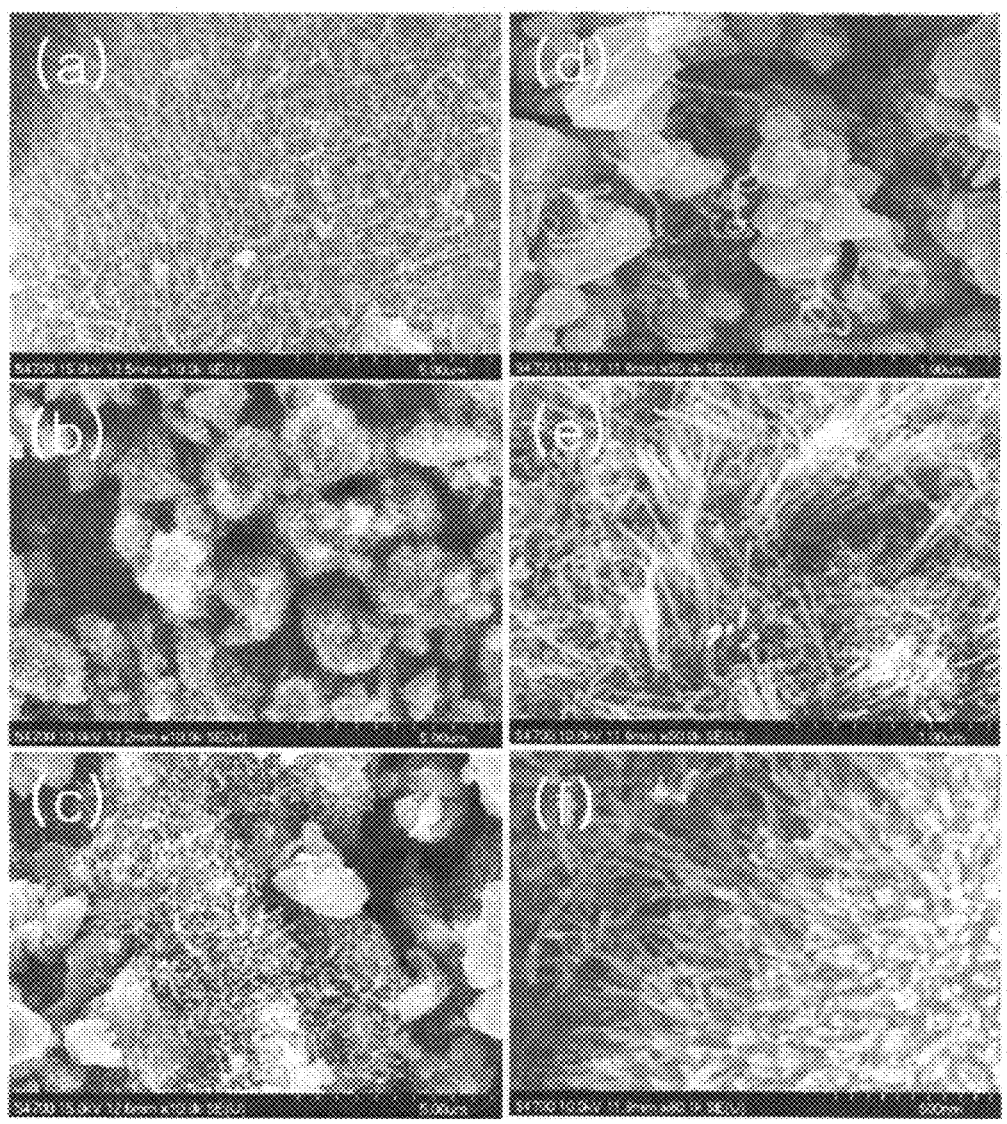
FIG. 22 shows the results of synthesizing the inventive single-crystal apatite nanowires sheathed in graphitic shells, on various substrates containing calcium.

Results of Synthesis of Single-Crystal Apatite Nanowires Sheathed in Graphitic Shells, on Various Substrates Containing Calcium FIG. 22 shows the results of synthesis of the inventive single-crystal apatite nanowires sheathed in graphitic shells, on various substrates containing calcium. In this Example, the following calcium-containing substrates were used: FIG. 22(a): an Si—Al—Ca—Na—O-based substrate; FIG. 22(b): an Si—Al—Ca—O-based substrate; FIG. 22(c): an Si—Ca—O-based substrate; FIG. 22(d): a Ca—C—O-based substrate; FIG. 22(e): a Ca—O-HA (hydroxyapatite)-based substrate; and FIG. 22(f): a Ca—O-A:C (amorphous carbon)-based substrate. As can be seen in FIG. 22, heterogeneous nanowires composed of crystalline graphitic shells and apatite cores were successfully synthesized using each of the substrate.

Example 22

Figure 23:
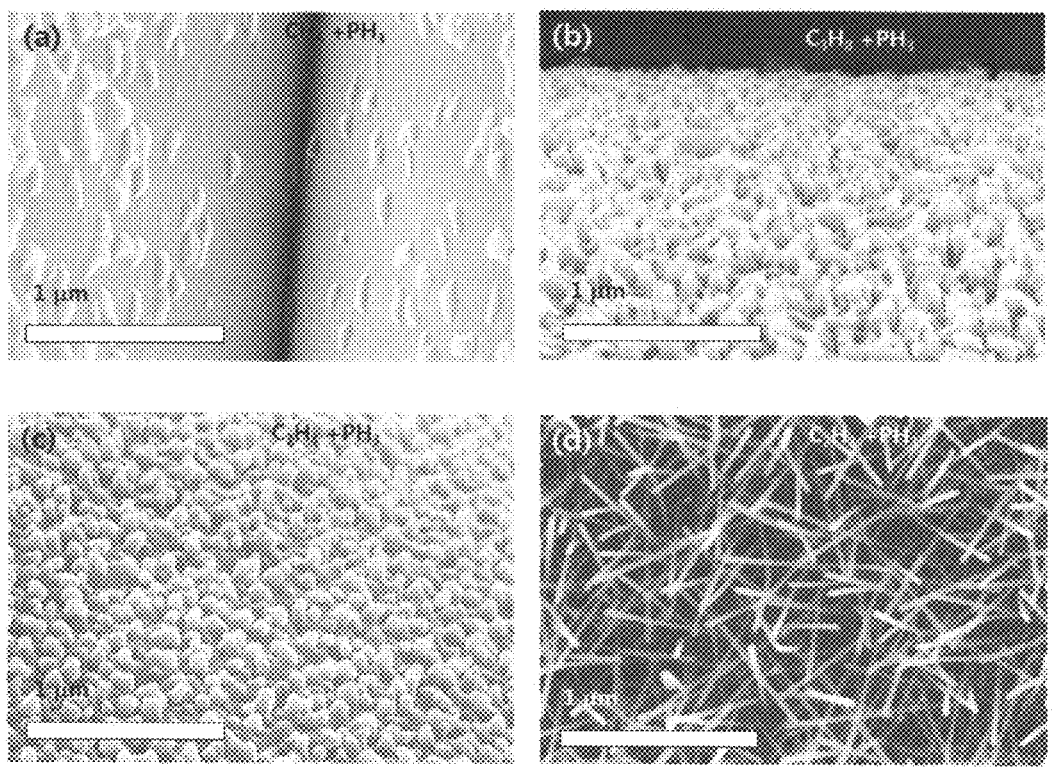
FIG. 23 shows the results of synthesizing the inventive single-crystal nanowires sheathed in graphitic shells using a variety of carbon source-containing reactant gases.

Results of Synthesis of Single-Crystal Apatite Nanowires Sheathed in Graphitic Shells as a Function of the Kind of Carbon Source-Containing Reactant Gas FIG. 23 shows the results of synthesis of the inventive single-crystal apatite nanowires sheathed in graphitic shells, as a function of the kind of carbon source-containing reactant gas. FIG. 23(a) shows the results obtained when methane ($CH_4$) was used as a carbon source. As can be seen therein, nanostructures are observed on the surface of glass fiber. However, the nanostructures were amorphous in nature and did not grow into nanowires. FIG. 23(b) shows the results obtained when ethylene ($C_2H_4$) was used as a carbon source. As can be seen therein, nanoparticles of uniform size are observed. However, these nanoparticles did not grow into nanowires. FIG. 23(c) shows the results obtained when propane ($C_3H_8$) was used as a carbon source. Some nanorod-type nanostructures appear in FIG. 23(c). Finally, FIG. 23(d) show the results obtained when acetylene ($C_2H_2$) was used as a carbon source. As can be seen therein, the nanostructures mostly grew into nanowires. Such results can be based on the results of gas analysis obtained during the synthesis process, and it could be seen that the amount of the carbon-phosphorous organic compound, phosphorine, in the reactants gas was higher in the order of FIGS. (d)>(c)>(b)>(a). This demonstrates that phosphorine plays a very important role in the oriented growth of apatite nanowires.

Example 23

Figure 24:
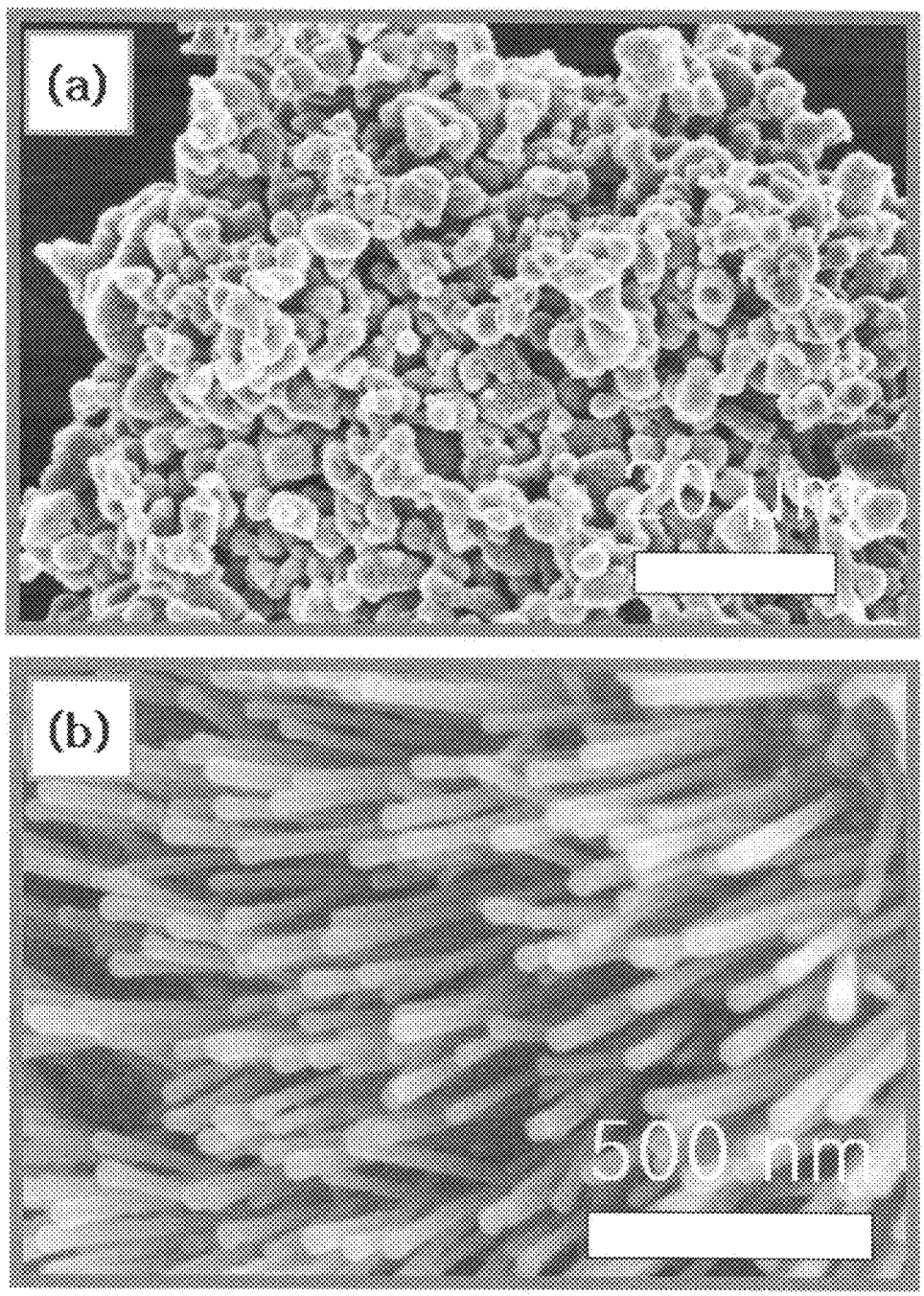
FIG. 24 shows an SEM image of the inventive single-crystal apatite nanowires sheathed in graphitic shells, grown on a strontium-containing substrate.

SEM Image of Single-Crystal Apatite Nanowires Sheathed in Graphitic Shells on Strontium-Containing Substrate FIG. 24 shows an SEM of the inventive single-crystal apatite nanowires sheathed in graphitic shells on a strontium-containing substrate. It was observed that the synthesized heterogeneous nanowires were distributed very uniformly on the strontium-containing glass powder. The heterogeneous nanowires appear to have a length of about 2 μm and a diameter of 50 nm or less. It was observed that the synthesized heterogeneous nanowires grew vertically on the surface of the strontium-containing glass powder.

Example 24

Figure 25:
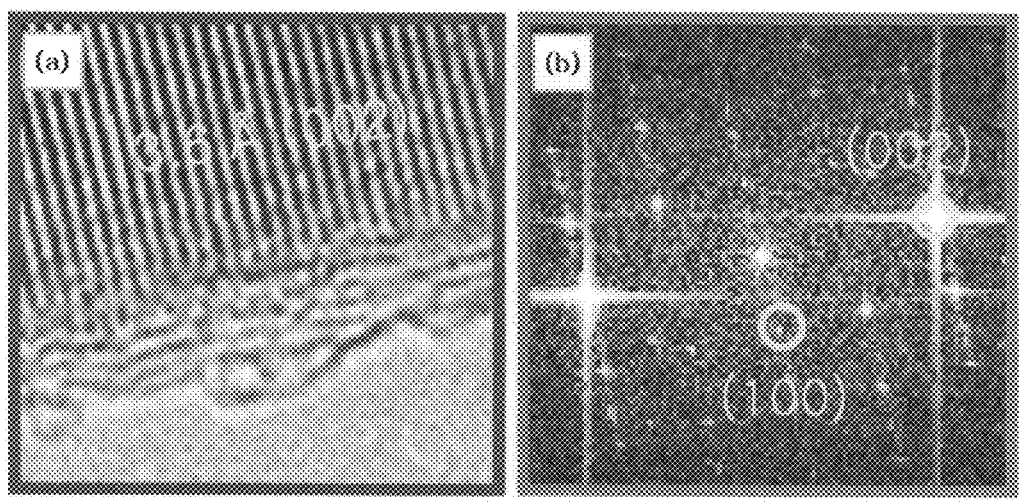
FIG. 25 shows a TEM image of the inventive single-crystal apatite nanowires sheathed in graphitic shells, grown on a strontium-containing substrate.

TEM Image of Single-Crystal Apatite Nanowires Sheathed in Graphitic Shells on Strontium-Containing Substrate FIG. 25 shows a TEM image of the inventive single-crystal apatite nanowires sheathed in graphitic shells on a strontium-containing substrate. It was observed that the heterogeneous nanowires were composed of inner nanowires sheathed in shells. It appears that the shells have a very small thickness of about 3 nm and the inner nanowire cores have a diameter of about 20 nm and are single-crystalline in nature. It was seen that the inner nanowire cores grew perpendicularly to the (002) plane of apatite. This result was evident from the additional analysis of diffraction pattern of the image. As shown in the high-magnification TEM image in FIG. 25(a), the material corresponding to the core was clearly single-crystalline in nature, and the direction of growth of the core was perpendicular to the (002) plane. The determined distance between the (002) planes was 0.36 nm, which is well consistent with that of the (002) plane of strontium apatite. The FFT diffraction pattern of the image is shown in FIG. 25(b). The (002) plane and the (100) plane perpendicular thereto are observed in FIG. 25(b). This is well consistent with the hexagonal structure of strontium apatite.

Example 25

Figure 26:
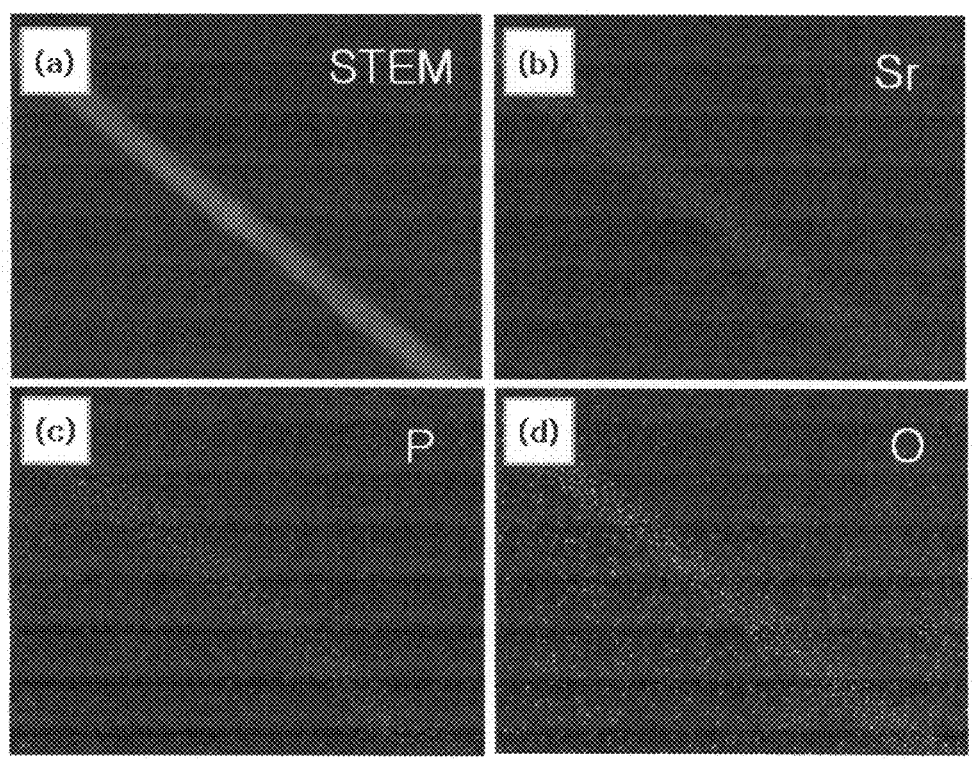
FIG. 26 shows an EDS of the inventive single-crystal apatite nanowires sheathed in graphitic shells, grown on a strontium-containing substrate.

Results of EDX Analysis of Single-Crystal Apatite Nanowires Sheathed in Graphitic Shells on Strontium-Containing Substrate FIG. 26 shows the results of EDX (scanning electron microscopy) of the inventive single-crystal apatite nanowires sheathed in graphitic shells on a strontium-containing substrate. As can be seen therein, strontium, phosphorus, oxygen and carbon were detected. Strontium, phosphorus and oxygen are the fundamental components of strontium apatite, and it was determined that carbon was detected in the amorphous carbon of the TEM grid and the crystalline carbon shell of the heterogeneous nanowires. Like the results of EDX of the synthesized nanowires, the results of EDX mapping revealed that strontium, phosphorus, oxygen and carbon which are the major components of strontium apatite were detected. In addition, it was shown that the ratio of the components was constant throughout the nanowires. This clearly demonstrates that the synthesized nanowires are composed of strontium cores and carbon shells.

As described above, the present invention provides the method of synthesizing heterogeneous nanowires composed of graphitic shells and apatite cores by introducing into a reactor either a material including an element corresponding to X in $X_5(YO_4)_3(Z)$, which is a chemical formula for apatite, or a substrate containing the material, continuously supplying carbon source- and phosphorous source-containing reactant gases into the reactor, and allowing the supplied reactant gases to react with the substrate. In addition, the method of the present invention has a very important significance in that it is very simple, and at the same time, makes it possible to achieve the simultaneous synthesis of graphitic shells and apatite cores, which has been considered difficult in the prior art, and it can synthesize graphitic shells and apatite cores in large amounts.

Graphitic shells have very versatile and excellent physical, mechanical, chemical and electrical properties, and apatite shows insufficient physical and mechanical properties, but has a very high biocompatibility. Thus, according to the core-shell structure of the present invention, the shortcomings of apatite can be significantly overcome by aid of graphitic sells while the excellent biocompatible properties thereof are maintained.

Such results suggest that the inventive heterogeneous nanowires composed of graphitic shells and apatite cores can be used as novel materials having excellent physical properties, in the nanotechnology field, the biotechnology field, and various-nano/bio-technology fields. In addition, the material and synthesis technology of the present invention can substitute for existing materials and synthesis technologies and can provide the opportunity of creating new markets.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A method for synthesizing single-crystal apatite nanowires sheathed in graphitic shells, the method comprising
   i) introducing into a reactor either a material including an element corresponding to X of $X_5(YO_4)_3(Z)$, which is a chemical formula for apatite, or a substrate containing the material;
   ii) maintaining the inside of the reactor in a vacuum and supplying a carrier gas to the reactor;
   iii) increasing the temperature of the reactor to synthesis temperature;
   iv) supplying reactant gases comprising carbon and phosphorus sources to the reactor and allowing the reactant gases to react with the material or substrate introduced into the reactor in step i); and
   v) cooling the reactor to room temperature in a carrier gas atmosphere.

2. The method of claim 1, wherein the substrate includes one or more selected from the group consisting of Ca, K, Na, Sr, Ba, Mg, Pb, Cb, and Zn, or oxides thereof, or materials capable of inducing them.

3. The method of claim 1, wherein the substrate is biomaterial containing calcium, in which the biomass material is selected from henequen and kenaf, which are woody biomasses, red algae and brown seaweed.

4. The method of claim 2, wherein the substrate has a shape selected from the group consisting of foam, mesh, sphere, fiber, tube, plate, thin film, powder and nanoparticle shapes.

5. The method of claim 1, wherein the temperature of the reactor is controlled to the synthesis temperature ranging from 500° C. to 1000° C. before the reactant gases are supplied, and the reaction time for synthesis is controlled within the range of 30 seconds to 2 hours.

6. The method of claim 1, wherein the carbon source-containing reactant gas that is supplied to the reactor includes a hydrocarbon gas selected from the group consisting of acetylene, ethylene, ethane, propane and methane, and the phosphorus source-containing reactant gas that is supplied to the reactor includes a phosphine gas.

7. The method of claim 1, wherein the carbon source- and phosphorus source-containing reactant gases which are supplied to the reactor induce carbon-phosphorous organic compounds, including phosphorine and phosphinoline, which play a key role in the nucleation and crystallization of apatite nanoparticles and in the orientation of the apatite nanoparticles to the nanowires.

8. The method of claim 7, wherein, when the carbon-phosphorous organic compounds are in liquid form, they are evaporated by heating or atomized by ultrasonic evaporation, before they are supplied to the reactor.

9. The method of claim 6, wherein the graphitic shells are formed on the radial surface of the apatite nanowires under supply of the carbon source, in which the formation of the graphitic shells around the apatite nanowires is performed by aromatic hydrocarbon molecules produced by cyclization of hydrocarbons supplied as the carbon source.

10. A method for synthesizing single-crystal apatite nanowires sheathed in graphitic shells, which have a lateral change along the axial direction thereof, the method comprising the steps of:
   i) introducing into a reactor either a material including an element corresponding to X of $X_5(YO_4)_3(Z)$, which is a chemical formula for apatite, or a substrate containing the material;
   ii) maintaining the inside of the reactor in a vacuum and supplying a carrier gas to the reactor;
   iii) increasing the temperature of the reactor to synthesis temperature;
   iv) supplying reactant gases comprising carbon and phosphorus sources into the reactor and allowing the reactant gases to react with the material or substrate, introduced into the reactor in step i);
   v) controlling any one or more of the temperature of the reaction between the reactant gases and the substrate, the reaction time, and the concentration of the carbon or phosphorus-containing reactant gases, thereby controlling the shape of the heterogeneous nanowires being synthesized; and
   vi) cooling the reactor to room temperature in a carrier gas atmosphere.

11. The method of claim 10, wherein, in the step of allowing the reactant gases to react with the substrate material, the supply of the carbon and phosphorus sources is changed with time, thereby controlling the length of knot-like portions which change the thickness of the nanowires along the axial direction of the nanowires, and the number of knot-like portions is controlled by controlling the number of changes in the supply of the carbon and phosphorus sources.

12. The method of claim 10, wherein, in the step of allowing the reactant gases to react with the substrate material, whether the graphitic shells are formed on the surface of the apatite cores is controlled by switching on or off the supply of the carbon source-containing reactant gas.

13. Single-crystal apatite nanowires sheathed in graphitic shells, synthesized according to a method as set forth in any one of claims 10 to 12, in which the nanowires have a lateral change along the axial direction thereof.

* * * * *